United States Patent
Loeffler et al.

(10) Patent No.: US 8,629,224 B2
(45) Date of Patent: Jan. 14, 2014

(54) WATER-SOLUBLE OR WATER-SWELLABLE POLYMERS ON THE BASIS OF SALTS OF ACRYLOYLDIMETHYLTAURINE ACID OR THE DERIVATIVES THEREOF, THE PRODUCTION THEREOF AND THE USE THEREOF AS THICKENER, STABILIZER AND CONSISTENCY AGENTS

(75) Inventors: Matthias Loeffler, Idstein (DE); Thomas Lindner, Mannheim (DE); Ute Back, Blankenbach (DE); Michael Hornung, Frankfurt am Main (DE)

(73) Assignee: Clariant Finance (BVI) Limited, Tortola (VG)

( * ) Notice: Subject to any disclaimer, the term of this patent is extended or adjusted under 35 U.S.C. 154(b) by 551 days.

(21) Appl. No.: 12/747,727

(22) PCT Filed: Dec. 16, 2008

(86) PCT No.: PCT/EP2008/010677
§ 371 (c)(1),
(2), (4) Date: Jun. 11, 2010

(87) PCT Pub. No.: WO2009/083130
PCT Pub. Date: Jul. 9, 2009

(65) Prior Publication Data
US 2010/0278763 A1    Nov. 4, 2010

(30) Foreign Application Priority Data
Dec. 21, 2007   (DE) .................. 10 2007 061 969

(51) Int. Cl.
| A61K 8/81 | (2006.01) |
| A61Q 17/04 | (2006.01) |
| A61Q 19/00 | (2006.01) |
| A61Q 19/02 | (2006.01) |
| A61Q 19/08 | (2006.01) |

(52) U.S. Cl.
USPC ............ 526/72; 526/264; 526/287; 526/288; 424/59; 424/70.9; 424/70.11

(58) Field of Classification Search
USPC .......... 424/59, 70.9, 70.11; 526/72, 264, 287, 526/288
See application file for complete search history.

(56) References Cited

U.S. PATENT DOCUMENTS

| 5,080,809 A * | 1/1992 | Stahl et al. ............. 507/221 |
| 5,736,125 A | 4/1998 | Morawsky et al. |
| 5,879,718 A | 3/1999 | Sebillote-Arnaud |
| 5,908,618 A | 6/1999 | Lorant |
| 6,054,138 A | 4/2000 | Trebose et al. |
| 6,083,491 A | 7/2000 | Mellul et al. |
| 6,120,780 A | 9/2000 | Dupis et al. |
| 6,355,752 B1 | 3/2002 | Brungs et al. |
| 6,380,137 B1 | 4/2002 | Heier et al. |
| 6,437,068 B2 | 8/2002 | Loeffler et al. |
| 6,468,549 B1 | 10/2002 | Dupis et al. |
| 6,620,420 B2 | 9/2003 | Lanzendorfer et al. |
| 6,645,476 B1 | 11/2003 | Morschhaeuser et al. |
| 6,696,517 B2 | 2/2004 | Loffler et al. |

(Continued)

FOREIGN PATENT DOCUMENTS

| CA | 2209060 | 12/1997 |
| DE | 19625810 | 1/1998 |

(Continued)

OTHER PUBLICATIONS

PCT International Search Report for PCT/EP2008/010677 mailed Mar. 11, 2009.

(Continued)

*Primary Examiner* — Richard Schnizer
*Assistant Examiner* — Alma Pipic
(74) *Attorney, Agent, or Firm* — Tod A. Waldrop

(57) ABSTRACT

Polymers are described comprising a) one or more of the recurring structural units of the formula (1)

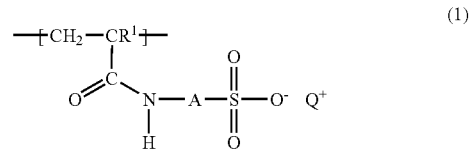

where $R^1$ is hydrogen, methyl or ethyl and A is $C_1$-$C_8$ alkylene, and $Q^+$ is $H^+$, $NH_4^+$, $Li^+$, $Na^+$, $K^+$, ½ $Ca^{++}$, ½ $Mg^{++}$, ½ $Zn^{++}$ or ⅓ $Al^{+++}$, and the neutralization degree of the structural units of formula (1) is 50 to 100 mol-%, and b) one or more of the recurring structural units of the formula (2)

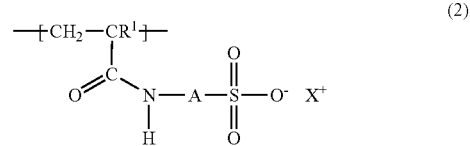

where $R^1$ and A are $R^1$ and A from formula (1) and $X^+$ is $[HNR^5R^6R^7]^+$, where $R^5$, $R^6$ and $R^7$ can independently from each other be hydrogen, a linear or branched alkyl group with 1 to 22 carbon atoms, a linear or branched, simple or polyunsaturated alkenylene group with 2 to 22 carbon atoms, a $C_6$-$C_{22}$-alkylamidopropyl group, a linear monohydroxyalkyl group with 2 to 10 carbon atoms or a linear or branched dihydroxyalkyl group with 3 to 10 carbon atoms, and wherein at least one of the groups $R^5$, $R^6$ and $R^7$ is not hydrogen.

17 Claims, No Drawings

(56) References Cited

U.S. PATENT DOCUMENTS

| | | |
|---|---|---|
| 6,872,228 B1 | 3/2005 | Lenzi-Brangi et al. |
| 7,081,507 B2 | 7/2006 | Morschhaeuser et al. |
| 7,186,405 B2 | 3/2007 | Loffler et al. |
| 7,279,154 B2 | 10/2007 | Loffler et al. |
| 7,332,155 B2 | 2/2008 | Loffler et al. |
| 7,393,520 B2 | 7/2008 | Loffler et al. |
| 7,399,478 B2 | 7/2008 | Loffler et al. |
| 8,211,414 B2 * | 7/2012 | Chen et al. ............... 424/70.16 |
| 2002/0176832 A1 | 11/2002 | Lanzendorfer et al. |
| 2004/0115157 A1 | 6/2004 | Loffler et al. |
| 2006/0110352 A1 | 5/2006 | Milbrandt et al. |
| 2007/0151044 A1 | 7/2007 | Cassier et al. |
| 2007/0248561 A1 | 10/2007 | Milbrandt et al. |

FOREIGN PATENT DOCUMENTS

| | | |
|---|---|---|
| DE | 10059826 | 6/2002 |
| DE | 10065046 | 6/2002 |
| DE | 10065047 | 7/2002 |
| DE | 102004002349 | 8/2005 |
| EP | 0504066 | 9/1992 |
| EP | 0510246 | 10/1992 |
| EP | 0815828 | 1/1998 |
| EP | 0816403 | 1/1998 |
| EP | 0850642 | 1/1998 |
| EP | 0815845 | 11/1998 |
| EP | 0815844 | 2/1999 |
| EP | 1028129 | 8/2000 |
| EP | 1033378 | 9/2000 |
| EP | 1069142 | 1/2001 |
| EP | 1116733 | 7/2001 |
| EP | 1251142 | 10/2002 |
| EP | 1676563 | 7/2006 |
| FR | 2875700 | 3/2006 |
| WO | WO 96/37180 | 11/1996 |
| WO | WO 98/00094 | 1/1998 |
| WO | WO 00/12053 | 3/2000 |
| WO | WO 02/43687 | 6/2002 |
| WO | WO 02/43688 | 6/2002 |
| WO | WO 02/44229 | 6/2002 |
| WO | WO 02/44270 | 6/2002 |
| WO | WO 02/44271 | 6/2002 |

OTHER PUBLICATIONS

International Preliminary Report On Patentability for PCT/EP2008/010677 mailed Aug. 19, 2010.
English Abstract for EP 1676563, Jul. 5, 2006.
English Abstract for FR 2875700, Mar. 31, 2006.

* cited by examiner

WATER-SOLUBLE OR WATER-SWELLABLE POLYMERS ON THE BASIS OF SALTS OF ACRYLOYLDIMETHYLTAURINE ACID OR THE DERIVATIVES THEREOF, THE PRODUCTION THEREOF AND THE USE THEREOF AS THICKENER, STABILIZER AND CONSISTENCY AGENTS

Water-soluble or water-swellable polymers on the basis of salts of acryloyldimethyltaurine acid or the derivatives thereof, the production thereof and the use thereof as thickener, stabilizer and consistency agents The present invention relates to crosslinked or noncrosslinked, water-soluble or water-swellable polymers based on salts of acrylamido-, methacrylamido- or ethacrylamido-alkylsulfonic acids, the counterions of said sulfonic acids representing mixtures of alkylammonium and other cations selected from $NH_4^+$, $Li^+$, $Na^+$, $K^+$, $Ca^{++}$, $Mg^{++}$, $Zn^{++}$, and $Al^{+++}$, and additionally, if desired, $H^+$, more particularly copolymers thereof with cyclic N-vinyl-carboxamides or cyclic and linear N-vinylcarboxamides, a process for preparing them, their use as a thickener, bodying agent, and stabilizer, more particularly their use as thickeners and bodying agents for aqueous systems and systems with a high fraction of oil components, and as stabilizers of emulsions and dispersions, more particularly of cosmetic, dermatological, and pharmaceutical compositions, and also cosmetic, dermatological, and pharmaceutical compositions comprising one or more of the polymers stated above.

For reasons of economics, technical performance or stability, water- or solvent-containing, multicomponent systems such as solutions, emulsions or suspensions are frequently adjusted to higher viscosities, or thickened. Thus, for example, by raising the viscosity of the external or internal phase of emulsions or suspensions, it is possible for the time before the components of such a system separate to be significantly extendable, which is manifested in an extension of the storage time. For numerous products, raising their viscosity also enhances their uniform spreadability, particularly on uneven surfaces. This is true in particular of skincare compositions and pharmaceutical ointments on the skin. For numerous technical products such as wallpaper removers, paint strippers or aircraft deicers, the increased viscosity prevents the product from running prematurely from the surface under treatment. The more uniform spread and prolonged period of action thus increase the activity. Besides the aforementioned performance advantages, the high viscosity of such products also offers further advantages in connection with production, packaging, dispensing, and storage, and also with transport; a particularly important application here, from a safety standpoint, is the thickening of acidic media.

Generally speaking, the rheological properties during production and/or formulation of cosmetic, dermatological, pharmaceutical or industrial products is a decisive criterion for the use of these products in practice. The thickeners employed are intended to produce adequate thickening in amounts that are as low as possible. However, the color and fundamental properties of the medium to be thickened are not to be altered.

Cosmetic skincare compositions such as creams and lotions are commonly in the form of oil-in-water or water-in-oil emulsions.

Oil-in-water emulsions are composed of an internal oil phase and an external, continuous water phase, which to stabilize the formulation is generally thickened using polymers. When applied, these emulsions give the skin a soft, caring, and pleasant feel.

The emulsions are generally further stabilized by incorporation of emulsifying surfactants of the oil-in-water (O/W) or water-in-oil (W/O) type. In order to achieve sufficient stability of the emulsions, however, surfactants of this kind must be added usually in amounts up to 10% by weight, based on the total weight of the emulsions. Emulsions without surfactants generally exhibit inadequate stabilization of the oil components, leading to the coagulation and separation of the oil phases.

One of the aims of skincare is to compensate the loss of oil and water from the skin that is caused by daily washing, to protect the skin from environmental effects, especially sun and wind, to provide a barrier to dirt, chemicals, and microorganisms, to counteract or compensate the loss of endogenous substances (e.g., water, natural fats, electrolytes), and to delay skin aging. For numerous applications, such as in baby care, for example, it is therefore useful to offer cosmetic skincare compositions with a very high fraction of oil components and skincare components. By a "very high oil fraction" is meant here a fraction of 35% by weight or more. The stabilization of a very high oil fraction poses an additional challenge; often, correspondingly high amounts of emulsifiers and stabilizers are used.

A disadvantage of the use of emulsifiers is that they can lead to irritation of the skin, the eyes, and the scalp, or even, in certain cases, may trigger an allergic reaction. It is known, for example, that certain emulsifiers, in conditions of simultaneous exposure to sunlight, may give rise to photodermatoses.

A further disadvantage is that high concentrations of emulsifier can lead to a rough, sticky or viscous feel to the compositions, or may make the compositions appear compact and heavy. Furthermore, the emulsifiers must be selected as a function of the polarity of the oils, meaning that the range of formulations is restricted.

Users of emulsions are therefore continually endeavoring to reduce the emulsifier content in order to improve the compatibility of the emulsions and to optimize their cosmetic properties.

In the course of recent years, polymers have become established on the market that permit the formulation of low-emulsifier emulsions or even of emulsifier-free emulsions (WO 96/37180 and U.S. Pat. No. 5,736,125). The polymers are hydrophobic modifications of conventional poly(meth)acrylates, with both thickening and emulsifying/dispersing properties. Examples of commercial products are Pemulen® TR-1 and TR-2 from Noveon and Aculyn® 22 and Aculyn® 28 from Rohm & Haas.

Since polymers with hydrophobic modification of this kind are based, without exception, on (meth)acrylic acid, they possess, accordingly, the disadvantages of the poly(meth)acrylates. One substantial disadvantage of thickeners based on poly(meth)acrylic acid is the heavy pH dependency of the thickening power. Thus, generally speaking, a sufficient viscosity is developed only when the pH of the formulation has been set to above 6.0 and the poly(meth)acrylic acid is therefore in neutralized form.

DE 44 25 268 describes emulsifier-free, finely disperse oil-in-water preparations which comprise acrylic acid polymers as thickeners, but which are likewise unsuitable for acidic formulations and are also unable to stabilize sizeable fractions of oil components.

EP-A-0 816 403 and WO 98/00094 describe crosslinked homopolymers of 2-acryl-amido-2-methylpropanesulfonates and their use as thickeners. EP-A-0 510 246 describes crosslinked copolymers of N-vinylcarboxamides and unsaturated alkylamides substituted with a sulfonate group, which are likewise suitable as thickeners. U.S. Pat. No. 5,080,809 describes noncrosslinked copolymers of N-vinylpyrrolidone and 2-acrylamido-2-methylpropanesulfonate. These polymers, however, are unsuitable for stabilizing relatively large fractions of oil without the addition of further emulsifiers.

EP 1 116 733 discloses water-soluble or water-swellable copolymers based on ammonium salts of acrylamidoalkylsulfonic acids and cyclic N-vinylcarboxamides or cyclic and linear N-vinylcarboxamides, their preparation, and their use as thickener/stabilizer of emulsions and dispersions. The polymers described in EP 1 116 733, however, are likewise unsuitable for stabilizing relatively large fractions of oil without the addition of further emulsifiers.

DE 100 65 047 and DE 100 65 046 describe cosmetic or dermatological gel creams of the oil-in-water type, or emulsions of the oil-in-water type, comprising ammonium acryloyldimethyltaurate/vinylpyrrolidone copolymers. These gel creams do not contain relatively large fractions of oil. Here again, in order to stabilize and thicken compositions with relatively large fractions of oil, it is necessary to use further emulsifiers.

The object, therefore, was to provide substances which can be used advantageously to produce compositions—for example, cosmetic, dermatological or pharmaceutical compositions—and by virtue of which it is possible to obtain compositions which, even with a high fraction of oil components and a low pH, exhibit very good rheological properties, at the same time are skin-friendly, and are also phase-stable without the use of emulsifiers or with a low level of emulsifier introduced.

Surprisingly it has now been found that this object is achieved by means of crosslinked and noncrosslinked, water-soluble or water-swellable polymers based on acrylamido-, methacrylamido- and/or ethacrylamido-alkylsulfonic acids, the counterions of said sulfonic acids representing mixtures of alkylammonium and other cations selected from $NH_4^+$, $Li^+$, $Na^+$, $K^+$, $Ca^{++}$, $Mg^{++}$, $Zn^{++}$, and $Al^{+++}$, and, if desired, $H^+$ as well, and more particularly the corresponding copolymers with cyclic N-vinyl-carboxamides or cyclic and linear N-vinylcarboxamides.

The invention provides polymers comprising a) one or more of the structural repeat units of the formula (1)

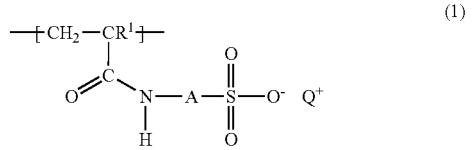

in which $R^1$ is hydrogen, methyl or ethyl and A is $C_1$-$C_3$-alkylene, and $Q^+$ is $H^+$, $NH_4^+$, $Li^+$, $Na^+$, $K^+$, ½ $Ca^{++}$, ½ $Mg^{++}$, ½ $Zn^{++}$ or ⅓ $Al^{+++}$, and the degree of neutralization of the structural units of the formula (1) is from 50 to 100 mol %, preferably from 80 to 100 mol %, more preferably from 90 to 100 mol %, and with more particular preference from 95 to 100 mol %, and b) one or more of the structural repeat units of the formula (2)

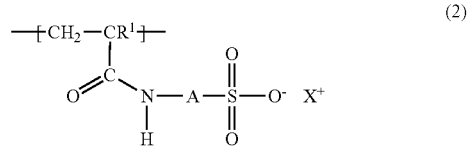

in which $R^1$ and A have the definition of $R^1$ and A from formula (1) and $X^+$ is $[HNR^5R^6R^7]^+$, where $R^5$, $R^6$, and $R^7$ independently of one another can be hydrogen, a linear or branched alkyl group having 1 to 22 carbon atoms, a linear or branched, singly or multiply unsaturated alkenyl group having 2 to 22 carbon atoms, a $C_6$-$C_{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals $R^5$, $R^6$, and $R^7$ is not hydrogen, with the proviso that the molar ratio of the structural units of the formula (1) in which $Q^+$ is $NH_4^+$, $Li^+$, $Na^+$, $K^+$, $Ca^{++}$, $Mg^{++}$, $Zn^{++}$ or $Al^{+++}$ to the structural units of the formula (2) is from 97:3 to 55:45, and the corresponding alkylammonium chlorides XCl possess a critical micelle concentration (CMC) <15 g/l, and d) 0% to 8%, preferably 0.01% to 5%, by weight of crosslinking structural units originating from monomers having at least two olefinic double bonds.

For the purposes of the present invention the cations $[HNR^5R^6R^7]^+$ are referred to as "alkylammonium". The compounds $NR^5R^6R^7$ are referred to in the context of the present invention as "alkylamine".

The degree of neutralization of the structural units of the formula (1) of x mol % means that in x mol % of the structural units of the formula (1) the definition of $Q^+$ is other than H.

The CMC is the concentration at which agglomerates (micelles) are formed. When the CMC is exceeded, above what is called a phase transition point, the profile of the physical properties of the solution undergoes a change with concentration, said properties including not least the surface tension or interfacial tension of the system. The CMC is determined by plotting the interfacial tension against the logarithm of the concentration.

The polymers of the invention are outstandingly suitable, among other things, as thickeners and bodying agents of aqueous systems, as stabilizers of emulsions and dispersions, more particularly of cosmetic, dermatological, and pharmaceutical compositions with a high oil fraction. In oil-in-water emulsions with a high oil fraction, even without the addition of surfactants or emulsifiers, they produce stable emulsions. Advantageously they also exhibit very good thickening properties over a wide pH range, in other words even in the presence of strongly acidic pH values.

One preferred embodiment of the invention are polymers comprising ab) 49.99% to 98.99% by weight of a mixture of the structural repeat units of the formulae (1) and (2), c1) 1% to 50% by weight of the structural repeat units of the formula (3)

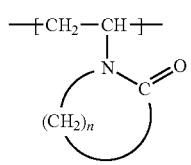

(3)

where n is an integer from 2 to 9,
or
c2) 1% to 50% by weight of a mixture of the structural repeat unit of the formula (3) and the structural repeat unit of the formula (4)

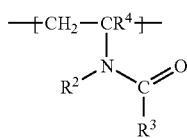

(4)

where $R^2$ and $R^3$ can be alike or different and are hydrogen or a linear or branched alkyl group having 1 to 22 carbon atoms or a linear or branched, singly or multiply unsaturated alkenyl group having 2 to 22 carbon atoms, and $R^4$ is hydrogen, methyl or ethyl
and
d) 0% to 8%, preferably 0.01% to 5%, by weight of crosslinking structural units originating from monomers having at least two olefinic double bonds.

Another preferred embodiment of the invention are polymers comprising
ab) 92% to 99.99% by weight of a mixture of the structural repeat units of the formulae (1) and (2) and
d) 8% to 0.01% by weight of crosslinking structural units originating from monomers having at least two olefinic double bonds.

Additionally preferred polymers of the invention comprise 69.5% to 97.5%, preferably 84.5% to 96.5%, by weight of a mixture of the structural units of the formulae (1) and (2), preferably derived from 2-acrylamido-2-methylpropane-sulfonic acid, 2% to 30%, preferably 3% to 15%, by weight of the structural units of the formula (3) or of a mixture of the structural units of the formulae (3) and (4), the structural units of the formula (3) being derived preferably from N-vinylpyrrolidone, and 0.2% to 3%, preferably 0.5% to 2%, by weight of crosslinking structural units originating from monomers having at least two olefinic double bonds. Among these polymers, preference is given in turn to those in which there are structural units of the formula (3) but there are no structural units of the formula (4).

In one particularly preferred embodiment of the invention the polymers of the invention are composed of 69.5% to 97.5% by weight of a mixture of the structural units of formulae (1) and (2), preferably derived from 2-acrylamido-2-methylpropane-sulfonic acid, 2% to 30% by weight of the structural units of the formula (3), preferably derived from N-vinylpyrrolidone, and 0.5% to 3% by weight of crosslinking structural units originating from monomers having at least two olefinic double bonds.

In one especially preferred embodiment of the invention the polymers of the invention are composed of 84.5% to 96.5% by weight of a mixture of the structural units of the formulae (1) and (2), preferably derived from 2-acrylamido-2-methylpropanesulfonic acid, 3% to 15% by weight of the structural units of the formula (3), preferably derived from N-vinylpyrrolidone, and 0.5% to 2% by weight of crosslinking structural units originating from monomers having at least two olefinic double bonds.

In the structural units of the formulae (1) and (2) of the polymers of the invention, $R^1$ is preferably hydrogen or methyl and more preferably hydrogen.

In the structural units of the formulae (1) and (2) of the polymers of the invention, A is preferably a structural unit of the formula $-CH_2-C(CH_3)_2-$.

With particular preference the structural units of the formulae (1) and (2) of the polymers of the invention are derived from 2-acrylamido-2-methylpropanesulfonic acid.

In the structural units of the formula (3) of the polymers of the invention, n is preferably 3, i.e., the structural units of the formula (3) are preferably derived from N-vinylpyrrolidone.

In the structural units of the formula (4) of the polymers of the invention, $R^2$ and $R^3$ are preferably hydrogen or methyl and $R^4$ is preferably hydrogen.

In the structural units of the formula (1) of the polymers of the invention the non-$H^+$ counterion $Q^+$ is preferably selected from $NH_4^+$, alkali metal$^+$, with $Na^+$ being preferred in turn among alkali metal$^+$, and alkaline earth metal$^{++}$. With particular preference the non-$H^+$ counterion $Q^+$ is $NH_4^+$.

In the structural units of the formula (2) of the polymers of the invention, the cation $X^+$ is preferably selected from laurylamidopropyldimethylammonium, stearylamidopropyldimethylammonium, behenylamidopropyldimethylammonium, $C_{12-18}$-alkyldimethylammonium, and $C_{20-22}$-alkyldimethylammonium.

The crosslinking structures of the polymers of the invention, originating from monomers having at least two olefinic double bonds, derive preferably from allyl acrylate, methacrylate or ethacrylate, more particularly from allyl acrylate or methacrylate; from dipropylene glycol diallyl ether, polyglycol diallyl ether, triethylene glycol divinyl ether, hydroquinone diallyl ether, tetraallyloxyethane or other allyl or vinyl ethers of polyfunctional alcohols, tetraethylene glycol diacrylate, triallylamine, trimethyiolpropane diallyl ether, trimethyloipropane triacryiate, methylenebis-acrylamide or divinylbenzene.

More preferably the crosslinking structures of the polymers of the invention derive from monomers of the formula (5)

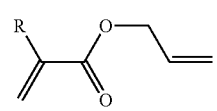

(5)

in which R is hydrogen, methyl or ethyl.

Additionally of particular preference as crosslinkers for the polymers of the invention are trimethylolpropane triacrylate (TMPTA) and methylenebisacrylamide (MBA). Trimethylolpropane triacrylate is particularly preferred.

In a further preferred embodiment of the invention the amount of the crosslinker used for preparing the polymers of the invention, based on the total mass of the monomers to be polymerized in the polymerization, is 0.01% to 8%, preferably 0.51% to 5%, more preferably 1% to 2.5%, and with more particular preference 1.2% to 2% by weight.

The distribution of the various structural units in the polymers of the invention may be random, blocklike, alternating or gradientlike.

The polymers of the invention preferably possess a molecular weight of $10^3$ to $10^9$ g/mol, more preferably of $10^4$ to $10^7$ g/mol, and with more particular preference of $5*10^5$ to $5*10^6$ g/mol.

The polymers of the invention are prepared, for example, by subjecting the monomers corresponding to the structural repeat units of the formulae (1) and (2), or (1), (2), (3), and, if desired, (4), to dispersion or dissolution in a protic solvent, preferably in tert-butanol, carrying out neutralization with a mixture of ammonia and/or a base containing $Li^+$, $Na^+$, $K^+$, $Ca^{++}$, $Mg^{++}$, $Zn^{++}$ or $Al^{+++}$, preferably of the corresponding hydroxides or carbonates, more preferably of the hydroxides, and with alkylamine, in the mixing ratio according to the invention, adding, if desired, one or more crosslinkers having at least two olefinic double bonds to this solution or dispersion, and initiating the polymerization in a conventional manner by adding a free-radical-forming compound.

The invention therefore further provides a process for preparing the polymers of the invention, which comprises
i) subjecting the monomers from which the structural units of the formulae (1) and (2) derive, and additionally, if desired, monomers from which the structural units of the formula (3) or of the formulae (3) and (4) derive, to dispersion or dissolution in a protic solvent,
ii) carrying out neutralization with ammonia or with a base containing $Li^+$, $Na^+$, $K^+$, $Ca^{++}$, $Mg^{++}$, $Zn^{++}$ or $Al^{+++}$, preferably of the corresponding hydroxides or carbonates, with particular preference the hydroxides, and with an alkylamine
iii) optionally adding one or more crosslinkers having at least two olefinic double bonds, and
iv) initiating the polymerization by adding a free-radical-forming compound.

For the application according to the invention it is very important that the above-mentioned molar ratio of the ions selected from $NH_4^+$, $Li^+$, $Na^+$, $K^+$, $Ca^{++}$, $Mg^{++}$, $Zn^{++}$, and $Al^{+++}$ to the alkylammonium ions of 97:3 to 55:45 is observed and that the critical micelle concentrations (CMC) of the corresponding hydrochloride salts of the amines employed, i.e., of the ammonium chlorides XCl, are below 15 g/l.

The polymers of the invention have an outstanding thickening ability, not only for compositions with an aqueous or aqueous-alcoholic basis but also for compositions with an aqueous-surfactant basis, but especially for compositions having a high oil fraction.

The polymers of the invention are advantageously suitable, moreover, as thickeners, bodying agents, emulsifiers, sensorial additives, solubilizers, dispersants, lubricants, tackifiers, and stabilizers.

The invention therefore further provides for the use of one or more of the polymers of the invention as thickener, bodying agent, emulsifier, sensorial additive, solubilizer, dispersant, lubricant, adhesive or stabilizer, preferably as a thickener, bodying agent or stabilizer, and, with particular preference, as a thickener.

The polymers of the invention are suitable more particularly as thickeners, bodying agents, emulsifiers, sensorial additives, solubilizers, dispersants, lubricants, tackifiers, and stabilizers, and preferably as thickeners, bodying agents or stabilizers, in compositions having a high fraction of oil components.

The polymers of the invention are suitable with exceptional preference for thickening compositions having a high fraction of oil components.

One preferred embodiment of the invention is therefore the use of one or more of the polymers of the invention as thickeners, bodying agents, emulsifiers, sensorial additives, solubilizers, dispersants, lubricants, tackifiers or stabilizers in compositions having an oil fraction of >5% by weight, preferably of 10% to 60% by weight, and more preferably of 20% to 45% by weight, based on the completed composition, preferably as thickeners, bodying agents or stabilizers, and more preferably as thickeners.

Oily substances may advantageously be selected from the groups of the triglycerides, natural and synthetic fatty substances, preferably esters of fatty acids with alcohols of low C number, such as with isopropanol, propylene glycol or glycerol, for example, or esters of fatty alcohols with alkanoic acids of low C number, or with fatty acids, or from the group of alkyl benzoates, preferably $C_{12}$-$C_{15}$ alkylbenzoates, and also natural or synthetic hydrocarbon oils.

Substances contemplated include triglycerides of linear or branched, saturated or unsaturated, optionally hydroxylated, $C_8$-$C_{30}$ fatty acids, especially vegetable oils, such as sunflower oil, corn oil, soybean oil, rice oil, jojoba oil, babassu oil, pumpkin oil, grapeseed oil, sesame oil, walnut oil, apricot oil, orange oil, wheatgerm oil, peach kernel oil, macadamia oil, avocado oil, sweet almond oil, lady's smock oil, castor oil, olive oil, peanut oil, rapeseed oil and coconut oil, and also synthetic triglyceride oils, an example being the commercial product Myritol® 318. Hydrogenated triglycerides are preferred as well. It is also possible to use oils of animal origin, examples being bovine tallow, perhydrosqualene, and lanolin.

A further class of preferred oily substances are the benzoic esters of linear or branched $C_{8-22}$ alkanols, examples being the commercial products Finsolv® SB (isostearyl benzoate), Finsolv® TN ($C_{12}$-$C_{15}$ alkylbenzoate), and Finsolv® EB (ethylhexyl benzoate).

A further class of preferred oily substances are the dialkyl ethers having a total of 12 to 36 carbon atoms, more particularly with 12 to 24 carbon atoms, such as, for example, di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-3-ethyldecyl ether, tert-butyl n-octyl ether, isopentyl n-octyl ether, 2-methylpentyl n-octyl ether, di-tert-butyl ether, and diisopentyl ether.

Also contemplated are branched saturated or unsaturated fatty alcohols having 6-30 carbon atoms, isostearyl alcohol, for example, and also Guerbet alcohols.

A further class of preferred oily substances are alkyl esters of hydroxycarboxylic acids. Preferred alkyl esters of hydroxycarboxylic acids are full esters of glycolic acid, lactic acid, malic acid, tartaric acid or citric acid. Further hydroxycarboxylic esters suitable in principle are esters of 3-hydroxypropionic acid, of tartronic acid, of D-gluconic acid, saccharic acid, mucic acid or glucuronic acid. Suitability as the alcohol component of these esters is possessed by primary, linear or branched aliphatic alcohols having 8 to 22 carbon atoms. Particular preference in this context is given to the esters of $C_{12}$-$C_{15}$ fatty alcohols. Esters of this type are available commercially, as for example under the trade name Cosmacol® from EniChem, Augusta Industriale.

A further class of preferred oily substances are dicarboxylic esters of linear or branched $C_2$-$C_{10}$ alkanols, such as di-n-butyl adipate (Cetiol® B), di(2-ethylhexyl) adipate and di(2-ethylhexyl) succinate, and also diol esters such as ethylene glycol dioleate, ethylene glycol diisotridecanoate, propylene glycol di(2-ethylhexanoate), propylene glycol diisostearate, propylene glycol dipelargonate, butanediol diisostearate, and neopentyl glycol dicaprylate, and also diisotridecyl azelaate.

Preferred oily substances are also symmetrical, unsymmetrical or cyclic esters of carbonic acid with fatty alcohols, glycerol carbonate or dicaprylyl carbonate (Cetiol® CC).

A further class of preferred oily substances are the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols.

A further class of preferred oily substances are hydrocarbon oils, examples being those having linear or branched, saturated or unsaturated $C_7$-$C_{40}$ carbon chains, such as, for example, petrolatum, dodecane, isododecane, cholesterol, lanolin, synthetic hydrocarbons such as polyolefins, especially polyisobutene, hydrogenated polyisobutene, polydecane, and also hexadecane, isohexadecane, paraffin oils, isoparaffin oils, examples being the commercial products of the Permethyl® series, squalene, squalene, and alicyclic hydrocarbons, such as the commercial product 1,3-di(2-ethylhexyl)cyclohexane (Cetiol® S), for example, ozokerite, and ceresin.

Silicone oils and silicone waxes are preferably dimethylpolysiloxanes and cyclomethicones, polydialkylsiloxanes $R_3SiO(R_2SiO)_xSiR_3$, where R is methyl or ethyl, more preferably methyl, and x is a number from 2 to 500, examples being the dimethicones available under the trade names VICASIL (General Electric Company), DOW CORNING 200, DOW CORNING 225, DOW CORNING 200 (Dow Corning Corporation), and also the dimethicones available as SilCare® Silicone 41M65, SilCare® Silicone 41M70, SilCare® Silicone 41M80 (Clariant), stearyldimethylpolysiloxane, $C_{20}$-$C_{24}$-alkyl-dimethylpolysiloxane, $C_{24}$-$C_{28}$-alkyl-dimethylpolysiloxane, and also the methicones available as SilCare® Silicone 41M40 and SilCare® Silicone 41M50 (Clariant), and additionally trimethylsiloxysilicates $[(CH_2)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, examples being the polymethyl-phenylsiloxanes available under the commercial designations SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones, and amino-, fatty acid-, alcohol-, polyether-, epoxy-, fluorine- and/or alkyl-modified silicone compounds, and also polyethersiloxane copolymers.

The polymers of the invention are notable for being mild to the skin and having a pleasant sensation on the skin, and are suitable as thickeners, bodying agents, emulsifiers, sensorial additives, solubilizers, dispersants, lubricants, tackifiers or stabilizers, preferably as thickeners, bodying agents or stabilizers, and more preferably as thickeners, in cosmetic, pharmaceutical or dermatological compositions.

The invention accordingly further provides for the use of one or more of the polymers of the invention as thickeners, bodying agents, emulsifiers, sensorial additives, solubilizers, dispersants, lubricants, tackifiers or stabilizers, preferably as thickeners, bodying agents or stabilizers, and more preferably as thickeners, in cosmetic, pharmaceutical or dermatological compositions. In one preferred embodiment of the invention these compositions have an oil fraction of >5% by weight, preferably of 10% to 60% by weight, and more preferably of 20% to 45% by weight, based on the completed composition.

The present invention further provides cosmetic, pharmaceutical or dermatological compositions comprising one or more polymers of the invention.

The cosmetic, pharmaceutical, and dermatological compositions of the invention comprise the polymers of the invention in amounts of preferably 0.05% to 10% by weight, more preferably of 0.1% to 5% by weight, and with particular preference of 0.5% to 2% by weight, based on the completed compositions.

The cosmetic, dermatological, and pharmaceutical compositions of the invention have viscosities preferably in the range from 500 to 300 000 mPa·s, more preferably in the range from 1000 to 250 000 mPa·s, with particular preference in the range from 2000 to 150 000 mPa·s, and with exceptional preference in the range from 3000 to 100 000 mPa·s (25° C., Brookfield RVT, T-C spindle at 5 rpm).

In a further preferred embodiment of the invention, the cosmetic, dermatological or pharmaceutical compositions of the invention are in the form of fluids, gels, oils, foams, sprays, lotions or creams.

The cosmetic, dermatological, and pharmaceutical compositions of the invention may be present on an aqueous or aqueous-alcoholic basis or in the form of oil-in-water emulsions.

In one especially preferred embodiment, the compositions of the invention are in the form of oil-in-water or water-in-oil emulsions, preferably in the form of cosmetic, pharmaceutical or dermatological emulsions of the oil-in-water type, and comprise, based on the total weight of the composition, a) up to 95%, preferably 60% to 92%, more preferably 70% to 90%, with particular preference 75% to 85%, by weight of a water phase, b) up to 60%, preferably 0.1 to 55%, more preferably 1% to 50%, with particular preference 3% to 45%, and with exceptional preference 5% to 40%, by weight of an oil phase, c) up to 15%, preferably 0.5 to 12%, more preferably 1% to 8%, with particular preference 1% to 5%, by weight of one or more emulsifiers, and d) 0.05% to 10%, more preferably 0.1% to 5%, with particular preference 0.5% to 2%, by weight of one or more of the polymers of the invention.

It is additionally advantageous that the polymers of the invention can be used even without the accompanying use of an additional co-emulsifier and/or without the accompanying use of an additional bodying agent. The accompanying use of co-emulsifiers and/or bodying agents is therefore not mandatory, but is possible. A combination with other known co-emulsifiers and/or bodying agents may be desirable for the purpose of setting specific cosmetic profiles and for exploiting synergistic effects.

It is additionally advantageous that the polymers of the invention can be used even without the accompanying use of an emulsifier or surfactant, especially in oil-in-water emulsions. In one especially preferred embodiment of the invention, therefore, the compositions of the invention are in the form of oil-in-water emulsions and contain no emulsifiers or surfactants; in other words, they take the form of oil-in-water emulsions without the addition of an emulsifier or surfactant.

In a further, especially preferred embodiment of the invention, the compositions of the invention take the form of gel creams of the oil-in-water type, preferably of cosmetic, pharmaceutical or dermatological gel creams of the oil-in-water type, and contain, based on the total weight of the composition, a) up to 95%, preferably 50% to 95%, more preferably 70% to 90%, with more particular preference 75% to 85%, by weight of a water phase, b) up to 60%, preferably 1% to 30%, more preferably 3% to 25%, with more particular preference 5% to 15%, by weight of an oil phase, c) 0.05% to 10%, more preferably 0.1% to 5%, with more particular preference 0.5% to 2%, by weight of one or more of the polymers of the invention.

Alcohols contemplated for the compositions of the invention that have an aqueous-alcoholic or alcoholic basis include all monohydric or polyhydric alcohols. Preferred alcohols are those having 1 to 4 carbon atoms such as ethanol, propanol, isopropanol, n-butanol, isobutanol, tert-butanol or glycerol, and also alkylene glycols, especially propylene, butylene or hexylene glycol, and mixtures of the stated alcohols. Further preferred alcohols are polyethylene glycols having a relative molecular mass below 2000. Preference is given more particularly to the use of polyethylene glycol having a relative molecular mass of between 200 and 600 and polyethylene glycol having a relative molecular mass of between 400 and 600.

The polymers of the invention are stable to acid and are suitable for use in cosmetic, pharmaceutical and/or dermatological compositions with a low pH, more particularly for the care and treatment of the skin of the body or face.

Established over the course of a few years has been the use of acidic additives in cosmetic or dermatological compositions. For anti-aging products in particular, the peeling and renewal of the topmost skin layers of the stratum corneum is an aim. This gentle peeling is carried out using hydroxy acids and keto acids, more particularly alpha hydroxy acids (AHAs) and beta hydroxy acids, which may be linear, branched or cyclic, saturated or unsaturated. Modern cosmetology has been concerned for a number of years with this category of chemical compounds. They include glycolic acid from sugar cane, lactic acid from sour milk, citric acid from citrus fruits, tartaric acid from wine, salicylic acid, and pyruvic acid from papaya fruits.

The use of acidic additives and their salts makes it necessary in some cases to adjust the pH of the cosmetic or dermatological compositions into a distinctly acidic range.

The compositions of the invention may further comprise one or more acidic organic actives; the concentration for use is typically in the range from 0.01% to 20% by weight, preferably in the range from 0.1% to 5% by weight. Actives contemplated include glycolic acid, lactic acid, citric acid, tartaric acid, mandelic acid, salicylic acid and alkylated salicylic acids, caffeic acid, ascorbic acid, pyruvic acid, oligooxa monocarboxylic and dicarboxylic acids, fumaric acid, retinoic acid, sulfonic acids, benzoic acid, kojic acid, fruit acid, malic acid, gluconic acid, galacturonic acid, ribonic acid, and all of their derivatives, polyglycolic diacids in free or partly neutralized form, vitamin C, vitamin C derivatives, dihydroxyacetone or skin-whitening actives such as arbutin or glycyrrhetinic acid and salts thereof.

In a further preferred embodiment of the invention, the compositions of the invention possess a pH of 2 to 6.5, preferably of 2 to 6 and more preferably of 3 to 6.

A further application-relevant advantage of the polymers of the invention is their outstanding thickener performance and stability even in the presence of electrolytes. They are suitable for adjusting the viscosity of compositions with a high electrolyte fraction, and produce preferably clear solutions.

Electrolytes employed are inorganic salts, preferably ammonium salts or metal salts, more preferably those of halides, examples being $CaCl_2$, $MgCl_2$, LiCl, KCl, NaCl, carbonates, hydrogen carbonates, phosphates, sulfates, nitrates, with particular preference sodium chloride, and/or organic salts, preferably ammonium salts or metal salts, more preferably those of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid or galacturonic acid.

As electrolyte, the compositions of the invention may also comprise mixtures of different salts.

In a further preferred embodiment of the invention, the compositions of the invention therefore comprise one or more electrolytes.

Also included among these are aqueous antiperspirant formulations comprising aluminum salts, preferably aluminum chlorohydrate or aluminum-zirconium complex salts.

The amount of the one or more electrolytes in the compositions of the invention, based on the total composition of the invention, is preferably from 0.1% to 20.0% by weight, more preferably from 0.2% to 10.0% by weight, and with particular preference from 0.5% to 5.0% by weight.

The polymers of the invention are compatible with organic components and are ideally suited to the thickening, emulsifying, and stabilizing of sunscreen formulations. Surprisingly it has been found that the polymers of the invention stabilize oil-in-water sunscreen formulations in particular, and have the effect, moreover, of improved sun protection factors (SPF) and improved water resistance.

In a further preferred embodiment of the invention, the compositions of the invention are in the form of sunscreen compositions comprising one or more sun protection filters for protecting the hair and the skin from UV rays.

Sun protection filters contemplated include 4-aminobenzoic acid, 3-(4'-trimethyl-ammonium)benzylideneboran-2-one methyl sulfate, camphor benzalkonium methosulfate, 3,3,5-trimethylcyclohexyl salicylate, 2-hydroxy-4-methoxybenzophenone, 2-phenylbenzimidazole-5-sulfonic acid and its potassium, sodium, and triethanolamine salts, 3,3'-(1,4-phenylenedimethine)bis(7,7-dimethyl-2-oxobicyclo-[2.2.1]-heptane-1-methanesulfonic acid) and its salts, 1-(4-tert-butylphenyl)-3-(4-methoxyphenyl)propane-1,3-dione, 3-(4'-sulfo)benzylidenebornan-2-one and its salts, 2-ethylhexyl 2-cyano-3,3-diphenylacrylate, polymers of N-[2(and 4)-(2-oxoborn-3-ylidenemethyl)benzyl]acrylamide, 2-ethylhexyl 4-methoxycinnamate, ethoxylated ethyl 4-aminobenzoate, isoamyl 4-methoxycinnamate, 2,4,6-tris[p-(2-ethylhexyloxy-carbonyl)anilino]-1,3,5-triazine, 2-(2H-benzotriazol-2-yl)-4-methyl-6-(2-methyl-3-(1,3,3,3-tetramethyl-1-(trimethylsilyloxy)disiloxanyl)propyl)phenol, 4,4'-[(6-[4-(1,1-dimethylethyl)aminocarbonyl)phenylamino]-1,3,5-triazin-2,4-yl)diimino]bis(benzoic acid 2-ethylhexyl ester), 3-benzophenone, 4-benzophenone (acid), 3-(4'-methyl-benzylidene)-D,L-camphor, 3-benzylidene camphor, 2-ethylhexyl salicylate, 2-ethylhexyl 4-dimethylaminobenzoate, hydroxy-4-methoxybenzophenone-5-sulfonic acid (sulfisobenzonum) and the sodium salt, 4-isopropylbenzyl salicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and its sodium, potassium, and triethanolamine salts, octylmethoxycinnamic acid, isopentyl-4-methoxycinnamic acid, isoamyl-p-methoxycinnamic acid, 2,4,6-trianilino(p-carbo-2'-ethylhexyl-1'-oxy)-1,3,5-triazine(octyl triazone), phenol, 2-2(2H-benzotriazol-2-yl)-4-methyl-6-(2-methyl-3-(1,3,3,3-tetramethyl-1-(trimethylsilyl(oxy)disiloxanyl)propyl (drometrizole trisiloxane)benzoic acid, 4,4-(6-(((1,1-dimethylethyl)amino)carbonyl)phenyl)amino)-1,3,5-triazine-2,4-diyl)diimino)bis,bis(2-ethylhexyl)ester)benzoic acid, 4,4-(6-(((1,1-dimethylethyl)amino)carbonyl)phenyl) amino)-1,3,5-triazine-2,4-diyl)diimino)bis,bis(2-ethylhexyl)ester), 3-(4'-methylbenzylidene)-D,L-camphor (4-methylbenzylidene camphor), benzylidene camphor sulfonic acid, octocrylene, polyacrylamidomethylbenzylidene camphor, 2-ethylhexyl salicylate (octyl salicylate), 2-ethylhexyl 4-dimethyl-aminobenzoate (octyl dimethyl PABA), PEG-25 PABA, 2-hydroxy-4-methoxybenzophenone-5-sulfonic acid (benzophenone-5) and the Na salt, 2,2'-methylenebis-6-(2H-benzotriazol-2yl)-4-(tetramethylbutyl)-1,1,3,3-phenol, sodium salt of 2,2'-bis(1,4-phenylene)-1H-benzimidazole-4,6-disulfonic acid, (1,3,5)-triazine-2,4-bis((4-(2-ethylhexyloxy)-2-hydroxy)phenyl)-6-(4-methoxyphenyl), 2-ethylhexyl 2-cyano-3,3-diphenyl-2-propenoate, glyceryl octanoate, dip-methoxycinnamic acid, p-aminobenzoic acid and its esters, 4-tert-butyl-4'-methoxydibenzoylmethane, 4-(2-β-glucopyranoxy)propoxy-2-hydroxybenzophenone, octyl salicylate, methyl-2,5-diisopropylcinnamic acid, cinoxate, dihydroxydimethoxybenzophenone, disodium salt of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl dimethoxybenzylidenedioxoimidazolidinepropionate, methylenebisbenzotriazolyltetramethylbutylphenol, phenyl dibenzimidazoletetrasulfonate, bis-ethylhexyloxyphenol-methoxyphenol-triazine, tetrahydroxybenzophenones, terephthalylidenedicamphorsulfonic acid, 2,4,6-tris[4,2-ethylhexyloxycarbonyl)anilino]-1,3,5-triazine, methyl-bis(trimethylsiloxy)silyl-isopentyltrimethoxycinnamic acid, amyl p-dimethylaminobenzoate, amyl p-dimethylaminobenzoate, 2-ethylhexyl p-dimethylaminobenzoate, isopropyl p-methoxycinnamic acid/diisopropylcinnamic ester, 2-ethylhexyl-p-methoxycinnamic acid, 2-hydroxy-4-methoxybenzophenone, 2-hydroxy-4-methoxybenzophenone-5-sulfoacid and the trihydrate, and also 2-hydroxy-4-methoxybenzophenone-5-sulfonate, sodium salt, and phenylbenzimidazolesulfonic acid.

The amount of the aforementioned sun protection filters (one or more compounds) in the compositions of the invention is preferably from 0.001% to 30%, more preferably from 0.05% to 20%, and with particular preference from 1% to 10%, by weight, based on the total weight of the completed composition.

As further auxiliaries and additives, the cosmetic, pharmaceutical, and dermatological compositions of the invention may comprise surfactants, emulsifiers, waxes, cationic polymers, film formers, further thickeners, gelling agents, superfatting agents, refatting agents, antimicrobial actives, biogenic actives, astringents, deodorants, antioxidants, humectants, solvents, silicone compounds, colorants, fragrances, preservatives, pearlescents, opacifiers and/or water-soluble silicones.

Surfactants which may be present include anionic, cationic, nonionic, ampholytic surfactants and/or betaine surfactants.

The total amount of the surfactants used in the cosmetic, pharmaceutical, and dermatological compositions of the invention, based on the completed compositions, is preferably from 1% to 70% by weight, more preferably from 5% to 40% by weight, and with particular preference from 10% to 35% by weight.

Preferred anionic surfactants are $(C_{10}-C_{22})$-alkyl carboxylates and alkylene carboxylates, alkyl ether carboxylates, fatty alcohol sulfates, fatty alcohol ether sulfates, alkylamide sulfates and alkylamide sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol phosphates, fatty alcohol ether phosphates, protein-fatty acid condensates, alkylmonoglyceride sulfates and alkylmonoglyceride sulfonates, alkylglyceride ether sulfonates, fatty acid methyltaurides, fatty acid sarcosinates, sulforicinoleates, acylglutamates and acylglycinates. These compounds and their mixtures are used in the form of their water-soluble or water-dispersible salts, examples being the sodium, potassium, magnesium, ammonium salts and mono-, di- and triethanolammonium and analogous alkylammonium salts.

The amount of the anionic surfactants in the cosmetic, pharmaceutical, and dermatological compositions of the invention is preferably from 2% to 30% by weight, more preferably from 5% to 25% by weight, and with particular preference from 12% to 22% by weight, based on the completed compositions.

Preferred cationic surfactants are quaternary ammonium salts, such as di-$(C_8-C_{22})$-alkyl-dimethylammonium chloride or bromide, preferably di-$(C_8-C_{22})$-alkyl-dimethyl-ammonium chloride or bromide; $(C_8-C_{22})$-alkyl-dimethylethylammonium chloride or bromide; $(C_8-C_{22})$-alkyl-trimethylammonium chloride or bromide, preferably cetyltrimethylammonium chloride or bromide and $(C_8-C_{22})$-alkyl-trimethylammonium chloride or bromide; $(C_{10}-C_{24})$-alkyl-dimethylbenzylammonium chloride or bromide, preferably $(C_{12}-C_{18})$-alkyl-dimethylbenzylammonium chloride, $(C_8-C_{22})$-alkyldimethyl-hydroxyethylammonium chloride, phosphate, sulfate, and lactate, $(C_8-C_{22})$-alkylamidopropyltrimethylammonium chloride and methosulfate, N,N-bis(2-$C_8-C_{22}$-alkanoyl-oxyethyl)-dimethylammonium chloride and methosulfate and N,N-bis(2-$C_8-C_{22}$-alkanoyl-oxyethyl) hydroxyethyl-methyl-ammonium chloride and methosulfate.

The amounts of the cationic surfactants in the cosmetic, pharmaceutical, and dermatological compositions of the invention is preferably from 0.1% to 10% by weight, more preferably from 0.5% to 7% by weight, and with particular preference from 1% to 5% by weight, based on the completed compositions.

Preferred nonionic surfactants are fatty alcohol ethoxylates (alkylpolyethylene glycols); alkylphenolpolyethylene glycols; fatty amine ethoxylates (alkylaminopolyethylene glycols); fatty acid ethoxylates (acylpolyethylene glycols); polypropylene glycol ethoxylates (Pluronics®); fatty acid alkanolamides (fatty acid amide polyethylene glycols); sucrose esters; sorbitol esters and sorbitan esters and their polyglycol ethers, and also $C_8-C_{22}$-alkylpolyglucosides.

The amount of the nonionic surfactants in the cosmetic, pharmaceutical, and dermatological compositions of the invention (in the case of the rinse-off products, for example) is preferably in the range from 1% to 20% by weight, more preferably from 2% to 10% by weight, and with particular preference from 3% to 7% by weight, based on the completed compositions.

The cosmetic, pharmaceutical, and dermatological compositions of the invention may further comprise amphoteric surfactants. These surfactants may be described as derivatives of long-chain secondary or tertiary amines which possess an alkyl group having 8 to 18 carbon atoms and in which a further group is substituted by an anionic group which imparts solubility in water, as for example by a carboxyl, sulfate or sulfonate group. Preferred amphoteric surfactants are N—$(C_{12}-C_{18})$-alkyl-β-aminopropionates and N—$(C_{12}-C_{18})$-alkyl-β-iminodipropionates in the form of alkali metal salts and mono-, di-, and trialkylammonium salts. Suitable further surfactants are also amine oxides. These are oxides of tertiary amines with a long-chain group of 8 to 18 carbon atoms and two usually short-chain alkyl groups with 1 to 4 carbon atoms. Preference is given here, for example, to the $C_{10}$ to $C_{18}$ alkyl-dimethylamine oxides, fatty acid amidoalkyldimethylamine oxide.

A further preferred group of surfactants are betaine surfactants, also called zwitterionic surfactants. These surfactants contain in the same molecule a cationic group, more particularly an ammonium group, and an anionic group, which may be a carboxylate group, sulfate group or sulfonate group. Suitable betaines are preferably alkyl betaines such as cocobetaine or fatty acid alkylamidopropyl betaines, examples being cocoacylamidopropyldimethyl betaine, or the $C_{12}$ to $C_{18}$ dimethylaminohexanoates and/or the $C_{10}$ to $C_{18}$ acylamidopropanedimethyl betaines.

The amount of the amphoteric surfactants and/or betaine surfactants in the cosmetic, pharmaceutical, and dermatological compositions of the invention is preferably from 0.5% to 20% by weight and more preferably from 1% to 10% by weight, based on the completed compositions.

Preferred surfactants are lauryl sulfate, laureth sulfate, cocoamidopropyl betaine, alkyl betaines such as, for example, coco-betaine, sodium cocoylglutamate, and lauroamphoacetate.

In a further preferred embodiment of the invention the cosmetic, pharmaceutical, and dermatological compositions of the invention further comprise, as foam boosters, co-surfactants from the group of alkyl betaines, alkylamido betaines, aminopropionates, aminoglycinates, imidazolinium betaines, and sulfo betaines, amine oxides, fatty acid alkanolamides, and polyhydroxyamides.

Cosmetic, pharmaceutical, and dermatological compositions of the invention in emulsion form may be produced without further emulsifier or else may comprise one or more emulsifiers. These emulsifiers may be selected from the group of nonionic, anionic, cationic or amphoteric emulsifiers.

Suitable nonionic emulsifiers are preferably as follows: adducts of 0 to 30 mol of ethylene oxide and/or 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan and/or sorbitol esters; ($C_{12}$-$C_{18}$) fatty acid monoesters and diesters of adducts of 0 to 30 mol of ethylene oxide with glycerol; glycerol mono esters and diesters and sorbitan monoesters and diesters of saturated and unsaturated fatty acids having 6 to 22 carbon atoms and, if desired, their ethylene oxide adducts; adducts of 15 to 60 mol of ethylene oxide with castor oil and/or hydrogenated castor oil; polyol esters and especially polyglycerol esters, such as polyglycerol polyricinoleate and polyglycerol poly-12-hydroxystearate, for example. Likewise suitable with preference are ethoxylated fatty amines, fatty acid amides, fatty acid alkanolamides, and mixtures of compounds from two or more of these classes of substance.

Examples of suitable ionogenic emulsifiers include anionic emulsifiers, such as mono-, di- or tri-phosphoric esters, soaps (e.g., sodium stearate), fatty alcohol sulfates, and also cationic emulsifiers such as mono-, di-, and tri-alkyl quats and their polymeric derivatives.

Amphoteric emulsifiers preferentially available are alkylaminoalkylcarboxylic acids, betaines, sulfo betaines, and imidazoline derivatives.

Used with particular preference are fatty alcohol ethoxylates selected from the group of ethoxylated stearyl alcohols, isostearyl alcohols, cetyl alcohols, isocetyl alcohols, oleyl alcohols, lauryl alcohols, isolauryl alcohols, and cetylstearyl alcohols.

As ethoxylated alkyl ether carboxylic acid or salts thereof it is possible with advantage to use sodium laureth-11-carboxylate.

As ethoxylated triglycerides it is possible with advantage to use polyethylene glycol(60) evening primrose glycerides.

It is of advantage, furthermore, to select the polyethylene glycol glycerol fatty acid esters from the group of polyethylene glycol(20) glyceryl laurate, polyethylene glycol(6) glyceryl caprate/caprinate, polyethylene glycol(20) glyceryl oleate, polyethylene glycol(20) glyceryl isostearate, and polyethylene glycol(18) glyceryl oleate/cocoate.

Particularly suitable among the sorbitan esters are polyethylene glycol(20) sorbitan monolaurate, polyethylene glycol (20) sorbitan monostearate, polyethylene glycol(20) sorbitan monoisostearate, polyethylene glycol(20) sorbitan monopalmitate, and polyethylene glycol(20) sorbitan monooleate.

Particularly advantageous emulsifiers are glyceryl monostearate, glyceryl monooleate, diglyceryl monostearate, glyceryl isostearate, polyglyceryl-3 oleate, polyglyceryl-3 diisostearate, polyglyceryl-4 isostearate, polyglyceryl-2 dipolyhydroxystearate, polyglyceryl-4 dipolyhydroxystearate, PEG-30-dipolyhydroxystearate, diisostearoylpolyglyceryl-3 diisostearate, glycol distearate, and polyglyceryl-3 dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol, and polyethylene glycol(2) stearyl ether (steareth-2), alkylmethicone copolyols and alkyldimethicone copolyols, especially cetyldimethicone copolyol and lauryl methicone copolyol.

The cosmetic, pharmaceutical, and dermatological compositions of the invention may comprise one or more of the emulsifiers in amounts of preferably 0.1% to 20% by weight, more preferably of 1% to 15% by weight, and with more particular preference of 3% to 10% by weight, based on the completed compositions.

The cosmetic, pharmaceutical, and dermatological compositions of the invention may comprise waxes, examples being paraffin waxes, microwaxes, and ozokerites, beeswax and its component fractions, and also beeswax derivatives, waxes from the group of homopolymeric polyethylenes or copolymers of α-olefins, and also natural waxes such as rice wax, candelilla wax, carnauba wax, Japan wax or shellac wax.

As stabilizers it is possible to use metal salts of fatty acids, such as magnesium, aluminum and/or zinc stearate, for example, preferably in amounts of 0.1% to 10% by weight, more preferably of 0.5% to 8% by weight, and with particular preference of 1% to 5% by weight, based on the completed compositions.

As cationic polymers, suitability is possessed by those under the INCI name "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG tridecyth (Salcare SC95), PVP-dimethylaminoethyl methacrylate copolymer, guar-hydroxypropyltriammonium chlorides, and also calcium alginate and ammonium alginate. Additionally it is possible to use cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethylenimines; cationic silicone polymers, such as amidomethicone for example, copolymers of adipic acid and dimethylaminohydroxy-propyldiethylenetriamine; polyaminopolyamide and cationic chitin derivatives, such as chitosan, for example.

The cosmetic, pharmaceutical, and dermatological compositions of the invention may comprise one or more of the abovementioned cationic polymers in amounts of preferably 0.1% to 5% by weight, more preferably of 0.2% to 3% by weight, and with particular preference of 0.5% to 2% by weight, based on the completed compositions.

Furthermore, the cosmetic, pharmaceutical and dermatological compositions of the invention may comprise film formers, which depending on the intended application are selected from salts of phenylbenzimidazolesulfonic acid, water-soluble polyurethanes, examples being $C_{10}$ polycarbamyl polyglyceryl esters, polyvinyl alcohol, water-soluble acrylic acid polymers/copolymers and their esters or salts, examples being partial ester copolymers of acrylic/methacrylic acid, water-soluble cellulose, examples being hydroxymethylcellulose, hydroxyethylcellulose, and hydroxypropylcellulose, water-soluble quaterniums, polyquaterniums, carboxyvinyl polymers, such as carbomers and their salts, polysaccharides, examples being polydextrose and glucan, vinyl acetate/crotonate, available for example under the trade name Aristoflex® A 60 (Clariant).

The cosmetic, pharmaceutical, and dermatological compositions of the invention may comprise one or more film formers in amounts of preferably 0.1% to 10% by weight, more preferably of 0.2% to 5% by weight, and with more particular preference of 0.5% to 3% by weight, based on the completed compositions.

The desired viscosity of the compositions of the invention can be set by addition of further thickeners and gelling agents. Those suitable are preferably cellulose ethers and other cellulose derivatives (e.g., carboxymethylcellulose, hydroxyethylcellulose), gelatin, starch and starch derivatives, sodium alginates, fatty acid polyethylene glycol esters, agar agar, tragacanth or dextrin derivatives, more particularly dextrin esters. Additionally suitable are metal salts of fatty acids, preferably having 12 to 22 carbon atoms, examples being sodium stearate, sodium palmitate, sodium laurate, sodium arachidates, sodium behenate, potassium stearate, potassium palmitate, sodium myristate, aluminum monostearate, hydroxy fatty acids, examples being 12-hydroxy-stearic acid, 16-hydroxyhexadecanoyl acid; fatty acid amides; fatty acid alkanolamides; dibenzalsorbitol and alcohol-soluble polyamides and polyacrylamides, or mixtures of these. Additionally it is possible for crosslinked and noncrosslinked polyacrylates such as carbomer or sodium polyacrylates to be used.

Preferably the cosmetic, pharmaceutical, and dermatological compositions of the invention contain 0.01% to 20% by weight, more preferably 0.1% to 10% by weight, with particular preference of 0.2% to 3% by weight, and with very particular preference of 0.4% to 2% by weight of thickeners and/or gelling agents.

As superfatting agents it is possible with preference to use lanolin and lecithin, unethoxylated and polyethoxylated or acylated lanolin derivatives and lecithin derivatives, polyol fatty acid esters, mono-, di-, and triglycerides and/or fatty acid alkanolamides, the latter serving simultaneously as foam stabilizers, which are used preferably in amounts of 0.01% to 10% by weight, more preferably of 0.1% to 5% by weight, and with particular preference of 0.5% to 3% by weight, based on the completed compositions.

Antimicrobial actives employed include cetyltrimethylammonium chloride, cetylpyridinium chloride, benzethonium chloride, diisobutylethoxyethyldimethylbenzylammonium chloride, sodium N-laurylsarcosinate, sodium N-palmethyl-sarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, such as L-lysine hexadecylamide, citrate heavy metal salts, salicylates, piroctose, especially zinc salts, pyrithiones and their heavy metal salts, especially zincpyrithione, zinc phenolsulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide and Octopirox®, iodopropynyl butylcarbamate, methylchloroisothiazolinone, methylisothiazolinone, methyldibromo glutaronitrile, AgCl, chloroxylenol, Na salt of diethylhexyl sulfosuccinate, sodium benzoate, and also phenoxyethanol, benzyl alcohol, phenoxyisopropanol, parabens, preferably butyl-, ethyl-, methyl- and propylparaben, and also their Na salts, pentanediol 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), Na salt of hydroxymethyl glycinate, hydroxyethylglycine of sorbic acid, and combinations of these active substances.

The cosmetic, pharmaceutical, and dermatological compositions of the invention contain the antimicrobial actives preferably in amounts of 0.001% to 5% by weight, more preferably of 0.01% to 3% by weight, and with particular preference of 0.1% to 2% by weight, based on the completed compositions.

The cosmetic, pharmaceutical, and dermatological compositions of the invention may further comprise biogenic actives, selected from plant extracts, such as aloe vera, for example, and also local anesthetics, antibiotics, antiinflammatories, antiallergics, corticosteroids, sebostatic agents, Bisabolol®, allantoin, Phytantriol®, proteins, vitamins selected from niacine, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as the sodium salt of the monophosphoric ester of ascorbic acid or as the magnesium salt of the phosphoric ester of ascorbic acid, tocopherol and tocopherol acetate, and also vitamin E and/or its derivatives.

The cosmetic, dermatological or pharmaceutical compositions of the invention may contain biogenic actives preferably in amounts of 0.001% to 5% by weight, more preferably of 0.01% to 3% by weight, and with particular preference of 0.1% to 2% by weight, based on the completed compositions.

The cosmetic, pharmaceutical, and dermatological compositions of the invention may comprise astringents, preferably magnesium oxide, aluminum oxide, titanium dioxide, zirconium dioxide, and zinc oxide, oxide hydrates, preferably aluminum oxide hydrate (boehmite), and hydroxides, preferably those of calcium, magnesium, aluminum, titanium, zirconium or zinc, and also aluminum chlorohydrates, preferably in amounts of 0% to 50% by weight, more preferably in amounts of 0.01% to 10% by weight, and with particular preference in amounts of 0.1% to 10% by weight. Preferred deodorant compounds are allantoin and bisabolol. They are used preferably in amounts of 0.0001% to 10% by weight.

The cosmetic, pharmaceutical, and dermatological compositions of the invention may comprise, as pigments/micropigments, and also as sun protection filters, microfine titanium dioxide, mica/titanium oxide, iron oxides, mica/iron oxide, zinc oxide, silicon oxides, Ultramarine blue, and chromium oxides.

The cosmetic, pharmaceutical, and dermatological compositions of the invention may comprise antioxidants, preferably selected from amino acids (e.g., glycine, histidine, tyrosine, tryptophan) and their derivatives, imidazoles (e.g., urocaninic acid) and their derivatives, peptides such as DL-carnosine, D-carnosine, L-carnosine and their derivatives (e.g., anserine), carotenoids, carotenes (e.g., α-carotene, β-carotene, lycopene) and their derivatives, chlorogenic acid and its derivatives, lipoic acid and its derivatives (e.g., dihydrolipoic acid), aurothioglucose, propyithiouracil, and other thiols (e.g., thioredoxin, glutathione, cysteine, cystine, cystamine and their glycosyl, N-acetyl, methyl, ethyl, propyl, amyl, butyl, and lauryl, palmitoyl, oleyl, γ-linoleyl, cholesteryl, and glyceryl esters) and also their salts, dilauryl thiodipropionate, distearyl thiodipropionate, thiodipropionic acid and derivatives thereof (e.g., esters, ethers, peptides, lipids, nucleotides, nucleosides, and salts), and also sulfoximine compounds (e.g., buthionine sulfoximine, homocysteine sulfoximine, buthionine sulfone, penta-, hexa-, heptathionine sulfoximine) in very low tolerable doses, and also (metal) chelators (e.g., α-hydroxy fatty acids, palmitic acid, phytic acid, lactoferrin), α-hydroxy acids (e.g., citric acid, lactic acid, malic acid), humic acid, bile acid, bile extracts, bilirubin, biliverdin, EDTA, EGTA and their derivatives, unsaturated fatty acids and their derivatives (e.g., γ-linolenic acid, linoleic acid, oleic acid), folic acid and derivatives thereof, ubiquinone and ubiquinol and their derivatives, vitamin C and derivatives (e.g., ascorbyl palmitate, Mg ascorbyl phosphate, ascorbyl acetate), tocopherols and derivatives (e.g., vitamin E acetate), vitamin A and derivatives (vitamin A palmitate), and also coniferyl benzoate of benzoin resin, rutic acid and its derivatives, α-glycosylrutin, ferulic acid, furfurylideneglucitol, carnosine, butylated hydroxytoluene, butylated hydroxyanisole, nordihydroguaiac resin acid, nordihydroguaiaretic acid, trihydroxybutyrophenone, uric acid and its derivatives, mannose and its derivatives, zinc and its derivatives (e.g., ZnO, $ZnSO_4$), selenium and its derivatives (e.g., selenium methionine), stilbenes and their derivatives (e.g., stilbene oxide, trans-stilbene oxide), superoxide dismutase and the inventively suitable derivatives (salts, esters, ethers, sugars, nucleotides, nucleosides, peptides, and lipids) of these stated substances.

The antioxidants may protect the skin and hair from oxidative stress. Preferred antioxidants are vitamin E and its derivatives and also vitamin A and its derivatives.

The amount of the one or more antioxidants in the cosmetic, pharmaceutical, and dermatological compositions of the invention is preferably 0.001% to 30% by weight, more preferably 0.05% to 20% by weight, and with particular preference 1% to 10% by weight, based on the total weight of the composition.

It is possible, furthermore, to employ humectants selected from the sodium salt of 2-pyrrolidone-5-carboxylate (NaPCA), guanidine; glycolic acid and its salts, lactic acid and its salts, glucosamines and their salts, lactamide monoethanolamine, acetamide monoethanolamine, urea, hydroxy acids, panthenol and its derivatives, examples being D-panthenol (R-2,4-dihydroxy-N-(3-hydroxypropyl)-3,3-dimethyl-butamide), DL-panthenol, calcium pantothenate, panthetin, pantothein, panthenyl ethyl ether, isopropyl palmitate, glycerol and/or sorbitol, preferably in amounts of 0.1% to 15% by weight and more preferably of 0.5% to 5% by weight, based on the completed compositions.

Further possible additives include silicone compounds, preferably dimethylpolysiloxane, methylphenylpolysiloxanes, cyclic silicones, and also amino-, fatty acid-, alcohol-, polyether-, epoxy-, fluorine- and/or alkyl-modified silicone compounds, examples being alkylsilicones SilCare® Silicone 41M10, SilCare® Silicone 41M15, SilCare® Silicone 41M20, SilCare® Silicone 41M30 (Clariant), alkyltrimethicones SilCare® 31M30, SilCare® 31M40, SilCare® 31M50, SilCare® 31M60 (Clariant), phenyltrimethicones SilCare® 15M30, SilCare® 15M40, SilCare® 15M50, SilCare® 15M60 (Clariant), polyalkylarylsiloxanes, and polyethersiloxane copolymers.

The cosmetic, pharmaceutical, and dermatological compositions of the invention may comprise the aforementioned silicone compounds preferably in amounts of 0.1% to 20% by weight, more preferably of 0.2% to 15% by weight, and with particular preference of 0.5% to 10% by weight, based on the completed compositions.

As fragrance oils or perfume oils it is possible to use individual odorant compounds, examples being the synthetic products of the ester, ether, aldehyde, ketone, alcohol, and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate, and benzyl salicylate. The ethers include, for example, benzyl ethyl ether; the aldehydes include, for example, the linear alkanals having 8 to 18 carbon atoms, citral, citronellal, citronellyloxyacetaldehyde, cyclamenaldehyde, hydroxycitronellal, lilial and bourgeonal; the ketones include, for example, the ionones, alpha-isomethylionone, and methyl cedryl ketone; the alcohols include anethol, citronellol, eugenol, geraniol, linalool, phenylethyl alcohol, and terpineol; and the hydrocarbons include primarily the terpenes and balsams. Preference is given to using mixtures of different odorants which in unison produce a pleasant fragrance note.

Perfume oils may also comprise natural odorant mixtures, of the kind obtainable from plant or animal sources, examples being pine oil, citrus oil, jasmine oil, lily oil, rose oil or ylang ylang oil. Essential oils of relatively low volatility, which are usually used as flavoring components, are also suitable as perfume oils, examples being sage oil, chamomile oil, oil of cloves, melissa oil, mint oil, oil of cinnamon leaves, linden blossom oil, oil of juniper berries, vetiver oil, olibanum oil, galbanum oil, and ladanum oil.

Suitable preservatives are preferably phenoxyethanol, parabens, pentanediol or sorbic acid. They are used preferably in amounts of 0.001% to 5% by weight, more preferably of 0.01% to 3% by weight, with particular preference of 0.1% to 2% by weight, based on the completed compositions of the invention.

As acids or alkalis for pH adjustment it is preferred to use mineral acids, especially HCl, inorganic bases, especially NaOH or KOH, and organic acids, especially citric acid.

In a further preferred embodiment of the invention the compositions of the invention possess a pH in the range from 2 to 12 and preferably in the range from 3 to 8.

The nature of the cosmetic, pharmaceutical and dermatological compositions of the invention is decidedly advantageous:
the emulsions are creamy and unguent and do not at all have the gelatinous or even gelatin-like appearance of certain prior-art emulsions, in which the external aqueous phase has undergone thickening.

The cosmetic sensation on the skin as well is very good: on application, the emulsion imparts a sensation of freshness and of comfort, having at the same time a rich and nourishing effect; it is soft and comfortable, and in no way sticky.

The examples and applications below are intended to illustrate the invention in greater detail, but without restricting it to them (all percentages are in percent by weight; % by weight).

PREPARATION EXAMPLE

Polymers 1 to 13 and 15 to 24 were prepared as for polymer 14. The amounts of the starting materials are apparent from table 1 for the crosslinked polymers and from table 2 for the noncrosslinked polymers.

Preparation of Polymer 14:

A 1000 ml flask with anchor stirrer, reflux condenser, internal thermometer, and inlet facilities for $N_2$ and $NH_3$ was charged with 490.5 g of tert-butanol. Then 80.0 g of 2-acrylamido-2-methylpropanesulfonic acid were introduced and were dispersed with vigorous stirring, the clouding of the solvent being retained. Then 14.0 g of $(C_{20}-C_{22})$-alkyl-dimethylamine were added. Over a period of 90 minutes, 5.9 g of ammonia were introduced into the gas space above the batch, and then stirring was continued for at least 30 minutes more, until a pH of 4-9 had come about. 4.22 g of N-vinylpyrrolidone and 1.6 g of trimethylolpropane triacrylate were added and the reservoir vessel was rinsed in each case with tert-butanol (approximately 6 ml) in order to minimize losses during the addition. The reaction mixture was then heated to a temperature of 60° C., and was rendered inert by simultaneous introduction of $N_2$. After the temperature of 60° C. had been reached, 2.6 g of dilauryl peroxide were added. The reaction set in immediately following addition of the initiator, this being apparent from an increase in the temperature and from the flocculation of the polymer. About 15 minutes after the onset of the polymerization reaction, the nitrogen feed was shut off. Approximately 30 minutes after addition of the initiator, the temperature reached a maximum (about 65-70° C.). A further 30 minutes after passing through this maximum, the mixture was heated to reflux and stirred under these conditions for two hours. Over the course of the reaction, the contents of the reaction vessel took on a porridgey consistency, but remained readily stirable. It was then cooled to room temperature and the solid was isolated by suction filtration. The paste was dried in a vacuum drying oven at 60-70° C. over 24 hours. This gave 92.2 g of a fine white powder.

Polymers were prepared in the same way, with the alkylamine and the ammonium:alkylammonium ratio in the polymer being varied.

Employed for comparison, moreover, were the commercial products Hostacerin® AMPS (as per EP 0 816 403) and Aristoflex® AVC (as per EP 1 116 733), both with an ammonium:alkylammonium ratio of 100:0 in the polymer.

TABLE 1

Polymers 1 to 18, crosslinked

| Ex. | Alkylamine | Alkylamine [g] | Alkylamine [mol %] | ATBS [g] | NVP [g] | TMPTA [g] | DLP [g] |
|---|---|---|---|---|---|---|---|
| Hostacerin ® AMPS EP 0 816 403 | Ammonia | | | | | | |
| Aristoflex ® AVC EP 1 116 733 | Ammonia | | | | | | |
| 1 | Ethanolamine | 1.19 | 5.0 | 80.00 | 4.22 | 1.60 | 1.00 |
| 2 | Ethanolamine | 2.38 | 10.0 | 80.00 | 4.22 | 1.60 | 1.00 |
| 3 | Ethanolamine | 4.76 | 20.0 | 80.00 | 4.22 | 1.60 | 1.00 |
| 4 | Ethanolamine | 11.91 | 50.0 | 80.00 | 4.22 | 1.60 | 1.00 |
| 5 | Octylamine | 1.00 | 2.0 | 80.00 | 4.22 | 1.60 | 1.00 |
| 6 | Octylamine | 2.52 | 5.0 | 80.00 | 4.22 | 1.60 | 1.00 |
| 7 | Octylamine | 5.04 | 10.0 | 80.00 | 4.22 | 1.60 | 1.00 |
| 8 | SAPDMA | 2.87 | 2.0 | 80.00 | 4.22 | 1.60 | 1.00 |
| 9 | SAPDMA | 7.18 | 5.0 | 80.00 | 4.22 | 1.60 | 1.00 |
| 10 | SAPDMA | 14.35 | 10.0 | 80.00 | 4.22 | 1.60 | 1.00 |
| 11 | SAPDMA | 28.70 | 20.0 | 80.00 | 4.22 | 1.60 | 1.00 |
| 12 | SAPDMA | 71.76 | 50.0 | 80.00 | 4.22 | 1.60 | 1.00 |
| 13 | $(C_{20}-C_{22})$-alkyl-dimethylamine | 6.83 | 5.0 | 80.00 | 4.22 | 1.60 | 1.00 |
| 14 | $(C_{20}-C_{22})$-alkyl-dimethylamine | 14.00 | 10.0 | 80.00 | 4.22 | 1.60 | 1.00 |
| 15 | $(C_{20}-C_{22})$-alkyl-dimethylamine | 27.30 | 20.0 | 80.00 | 4.22 | 1.60 | 1.00 |
| 16 | $(C_{20}-C_{22})$-alkyl-dimethylamine | 68.25 | 50.0 | 80.00 | 4.22 | 1.60 | 1.00 |
| 17 | $(C_{20}-C_{22})$-alkyl-dimethylamine | 27.30 | 20.0 | 84.22 | — | 1.60 | 1.00 |
| 18 | $(C_{20}-C_{22})$-alkyl-dimethylamine | 68.25 | 10.0 | 84.22 | — | 1.60 | 1.00 |

TABLE 2

Polymers 19 to 24, noncrosslinked

Composition

| Ex. | Alkylamine | Alkylamine [g] | Alkylamine [mol %] | ATBS [g] | NVP [g] | TMPTA [g] | DLP [g] |
|---|---|---|---|---|---|---|---|
| 19 | SAPDMA | 7.18 | 5.0 | 80.00 | 4.22 | — | 1.00 |
| 20 | SAPDMA | 14.35 | 10.0 | 80.00 | 4.22 | — | 1.00 |
| 21 | $(C_{20}$-$C_{22})$-alkyl-dimethylamine | 6.83 | 5.0 | 80.00 | 4.22 | — | 1.00 |
| 22 | $(C_{20}$-$C_{22})$-alkyl-dimethylamine | 14.00 | 10.0 | 80.00 | 4.22 | — | 1.00 |
| 23 | SAPDMA | 14.35 | 10.0 | 84.22 | — | — | 1.00 |
| 24 | $(C_{20}$-$C_{22})$-alkyl-dimethylamine | 6.83 | 5.0 | 84.22 | — | — | 1.00 |

ATBS: 2-Acrylamido-2-methylpropanesulfonic acid
NVP: N-Vinylpyrrolidone
TMPTA: Trimethylolpropane triacrylate
DLP: Dilauryl peroxide
SAPDMA: Stearylamidopropyldimethylamine ex Goldschmidt
$(C_{20}$-$C_{22})$-alkyl-dimethylamine: Genamin ® 20/22 R302D - ex Clariant
Octylamine: ex Aldrich
Monoethanolamine: ex Merck The values for alkylamine in mol % that are indicated in tables 1 and 2 are based on the total amount of ammonia and alkylamine. For example, 10.0 mol % of alkylamine for polymer 14 in table 1 means that, based on the total amount of ammonia and alkylamine, 10.0 mol % of alkylamine and 90.0 mol % of ammonia were used in preparing the polymer.

For the purposes of the present invention the CMC measurements are carried out in accordance with ISO 4311 ("anionic and non-ionic surface active agents—determination of the critical micellization concentration—method by measuring surface tension with a plate, stirrup or ring"). Aqueous solutions of the alkylamines are adjusted with HCl to a pH of 5.0-6.0. The CMCs of the corresponding hydrochlorides are measured on a KRÜSS plate tensiometer.

Monoethanolamine hydrochloride
No CMC, not surface-active

Stearylamidopropyldimethylamine (SAPDMA) hydrochloride
CMC: 0.06 g/l $(C_{20}$-$C_{22})$-Alkyl-dimethylamine hydrochloride
CMC: 0.12 g/l Octylamine hydrochloride CMC: 20.0 g/l The copolymers of the invention were thereafter tested for their suitability as thickeners and bodying agents. As a test system with a high oil fraction, without the addition of emulsifier, the following composition was selected:

43% liquid paraffin
0.8% Phenonip XB
0.35% polymer from table 1
1% glycerol
ad 100% water Phenonip XB: phenoxyethanol (and) methylparaben (and) ethylparaben (and) propylparaben

TABLE 3

Viscosity capacity, emulsifying capacity, and stability behavior

| Emulsion containing polymer | Viscosity 0.5% in H$_2$O [mPa·s] | Viscosity 1.0% in H$_2$O [mPa·s] | Emulsifying capacity | Viscosity emulsion [mPa·s] | Stability −5° C./+40° C. | Stability +50° C. |
|---|---|---|---|---|---|---|
| Hostacerin ® AMPS | 16 000 | 54 500 | no | | | |
| Aristoflex ® AVC | 17 500 | 51 000 | no | | | |
| 1 | 25 000 | 40 600 | no | | | |
| 2 | 21 600 | 27 400 | no | | | |
| 3 | 18 850 | 23 050 | no | | | |
| 4 | 1035 | 2135 | no | | | |
| 5 | 26 500 | 61 000 | no | | | |
| 6 | 24 400 | 45 200 | no | | | |
| 7 | 16 850 | 20 700 | no | | | |
| 8 | 16 750 | 14 620 | no | | | |
| 9 | 26 850 | 56 600 | yes | 4000 | 7 cycles | 7 weeks |
| 10 | 14 960 | 33 200 | yes | 4500 | 7 cycles | 7 weeks |
| 11 | 4360 | 13 050 | yes | 3500 | 14 cycles | 7 weeks |

TABLE 3-continued

Viscosity capacity, emulsifying capacity, and stability behavior

| Emulsion containing polymer | Viscosity 0.5% in H$_2$O [mPa · s] | Viscosity 1.0% in H$_2$O [mPa · s] | Emulsifying capacity | Viscosity emulsion [mPa · s] | Stability −5° C./+40° C. | Stability +50° C. |
|---|---|---|---|---|---|---|
| 12 | Not soluble | | no | | | |
| 13 | 16 100 | 51 200 | yes | 8000 | 14 cycles | >7 weeks |
| 14 | 9060 | 32 800 | yes | 9100 | 14 cycles | >7 weeks |
| 15 | 2280 | 14 300 | yes | 7000 | 7 cycles | >7 weeks |
| 16 | Not soluble | | no | | | |
| 17 | 6500 | 54 500 | yes | 9000 | 7 cycles | >7 weeks |
| 18 | 7000 | 49 000 | yes | 10 500 | 14 cycles | >7 weeks |

Comparison Polymers:

Hostacerin® AMPS (INCI: Ammonium Polyacryldimethyltauramide)

Aristoflex® AVC (INCI: Ammonium Acryloyldimethyltaurate/VP Copolymer)

Polymers 1-4 (alkylamine not surface-active, CMC of the ethanolamine hydrochloride>>15 g/l)

Polymers 5-7 (CMC of the octylamine hydrochloride>15 g/l)

Polymer 8 (CMC of the alkylamine hydrochloride<15 g/l, but molar ratio of ammonium:alkylammonium greater than 97:3)

Polymers 12, 16 (CMC of the alkylamine hydrochloride<15 g/l, but molar ratio of ammonium:alkylammonium less than 55:45)

Polymers of the Invention:

Polymers 9-11, 13-15, 17-24 (CMC of the alkylamine hydrochloride<15, molar ratio of ammonium:alkylammonium between 97:3 to 55:45)

Testing of the polymers as per table 3 showed that the polymers of the invention are outstandingly suitable for use as thickeners and bodying agents in aqueous systems, as stabilizers in emulsions and dispersions, especially in cosmetic, dermatological, and pharmaceutical compositions with a high oil fraction.

In particular it was found, surprisingly, that the polymers of the invention stabilize oil-in-water emulsions having a high oil fraction even without addition of emulsifiers.

TABLE 4

Storage stabilities of formulations I to IV

| Ingredients | I | II | III | IV |
|---|---|---|---|---|
| Water, deionized | ad 100% | ad 100% | ad 100% | ad 100% |
| Glycerol | 20 | 3 | 1 | 1 |
| Niacinamide | 5 | 1 | 1 | 1 |
| Panthenol | 1 | 0.1 | 0.1 | 0.1 |
| Isohexadecane | 6 | 20 | 6 | — |
| Ethylparaben | 0.15 | 0.15 | 0.15 | 0.15 |
| Coconut oil | 4 | 4 | 4 | — |
| Petrolatum | 2 | 20 | 6 | 43 |
| Propylparaben | 0.1 | 0.1 | 0.1 | 0.1 |
| PEG-100 stearate | 0.3 | 0.3 | 0.3 | — |
| Stearyl alcohol | 0.6 | 0.6 | 0.6 | — |
| Cetyl alcohol | 0.5 | 0.5 | 0.5 | — |
| Behenyl alcohol | 0.4 | 0.4 | 0.4 | — |
| Tocopherol acetate | 0.5 | 0.5 | 0.5 | 0.5 |
| Stearic acid | 0.1 | — | 0.1 | — |
| Polymer ex. 14 | 1 | 0.35 | — | 0.35 |
| Polymer ex. 10 | — | — | 0.35 | — |
| Sorbitan sesquiolate | — | — | 0.1 | 0.1 |
| NaOH | 0.011 | — | — | — |
| Dry Flo Plus | 2 | 2 | 2 | — |
| Benzyl alcohol | 0.25 | 0.25 | 0.25 | 0.25 |
| Cyclopentasiloxane | 1.5 | 1.5 | 1.5 | — |
| Perfume | 0.3 | 0.3 | 0.3 | 0.3 |
| Viscosity [mPa · s] | 25 000 | 35 000 | 18 000 | 30 000 |
| pH | 5.5 | 5.5 | 5.5 | 5.5 |
| Stability (90 days, 45° C.) | stable | stable | stable | stable |
| Stability(−5° C.-40° C., 5 cycles each of 24 h) | stable | stable | stable | stable |

APPLICATION EXAMPLES

Example 1

O/W Skin Milk

| | | |
|---|---|---|
| A | Polymer ex. 15 | 0.50% |
| | Isopropyl palmitate | 4.00% |
| | Almond oil | 4.00% |
| | Wheatgerm oil | 1.00% |
| | Cetiol ® SN (Henkel) (cetearyl isononanoate) | 8.00% |
| B | Aristoflex ® AVC (Clariant) (ammonium acryloyldimethyltaurate/VP copolymer) | 0.30% |
| C | Water | ad 100% |
| D | Fragrances | 0.30% |

Preparation

I Mix A and B, then add C
II Stir D into I
III Homogenize emulsion

Polymer ex. 15 is used as an emulsifier and also increases the consistency.

Example 2

O/W After-Sun Milk

| | | |
|---|---|---|
| A | Polymer ex. 13 | 0.50% |
| | Isopropyl palmitate | 15.00% |
| | Cetiol ® SN (Henkel) (cetearyl isononanoate) | 15.00% |
| | Soybean oil | 4.00% |

-continued

| | | |
|---|---|---|
| | Miglyol ® 812 (Dynamit Nobel) (caprylic/capric triglycerides) | 3.00% |
| | Jojoba oil | 3.00% |
| | Wheatgerm oil | 1.00% |
| B | AQUAMOLLIN ® BC powder, highly conc. (Clariant) Ethylenediaminetetraacetate, Na salt | 0.10% |
| | Citric acid (10% strength) | 0.30% |
| | Water | ad 100% |
| | Glycerol | 3.00% |
| | ALLANTOIN (Clariant) (Allantoin) | 0.20% |
| | Preservative | q.s. |
| C | Ethanol | 1.50% |
| | Perfume oil | 0.30% |

Preparation
I Stir the components of A together homogeneously
II At about 35° C., stir B into I. Finally add C
III Homogenize the emulsion Polymer ex. 13 serves as an emulsifier and thickener. In addition a soft, velvety sensation is produced on the skin.

Example 3

W/O Cream

| | | |
|---|---|---|
| A | HOSTACERIN ® DGI (Clariant) (polyglyceryl-2 sesquiisostearate) | 4.00% |
| | Beeswax | 2.00% |
| | Polymer ex. 11 | 1.50% |
| | Mineral oil, low viscosity | 5.00% |
| | Petrolatum | 10.00% |
| | Cetiol ® V (Henkel KGaA) (decyl oleate) | 5.00% |
| B | 1,2-Propylene glycol | 3.00% |
| | Water | ad 100% |
| | Preservative | q.s. |
| C | Fragrance | 0.40% |

Preparation
I Melt A at 80° C.
II Heat B to 80° C.
III Stir II into I
IV Cool with stirring
V At 35° C., add C to IV Polymer ex. 11 is used as a bodying agent and stabilizer.

Example 4

Hair Gel with Conditioning Properties

| | | |
|---|---|---|
| A | Water | ad 100% |
| | Panthenol | 1.50% |
| | UVAsorb S5 (Benzophenone-4) | 0.05% |
| | Dye solution | q.s. |
| | Preservative | q.s. |
| B | Emulsogen ® HCO 040 (Clariant) (PEG-40, hydrogenated castor oil) | 0.50% |
| | Perfume | q.s. |
| C | Polymer ex. 9 | 2.00% |
| D | Gafquat 755N (ISP) (Polyquaternium-11) | 2.50% |

Preparation
I Mix components A
II Mix components B and add to I
III Add C to D
IV Stir III into II Polymer ex. 9 acts as an efficient thickener with, in addition, conditioning properties.

Example 9

Hair Gel with Strong Hold

| | | |
|---|---|---|
| A | Water | ad 100% |
| | PVP K-30 (ISP) PVP | 4.00% |
| | Ethanol | 30.00% |
| | Panthenol | 0.50% |
| | UVAsorb S5 (Benzophenone-4) | 0.05% |
| | Dye solution | q.s. |
| | Preservative | q.s. |
| B | Abil B 8851 (Goldschmidt) (dimethicone copolyol) | 1.00% |
| | Emulsogen ® HCO 040 (Clariant) (PEG-40 hydrogenated castor oil) | 0.50% |
| | Fragrance | q.s. |
| C | Polymer ex. 15 | 2.50% |

Preparation
I Mix components A
II Add components B to I
III Add components C to I Polymer ex. 15 is used as a thickener with very good alcohol tolerance and serves, moreover, as a suspension agent and stabilizer for the insoluble oil fractions.

Example 10

O/W Skin Milk with Keratolytic Effect

| | | |
|---|---|---|
| A | Mineral oil | 4.00% |
| | Almond oil | 4.00% |
| | Cetiol ® SN (Henkel) (cetearyl isononanoate) | 8.00% |
| | Cetyl alcohol | 2.00% |
| | Stearic acid | 2.00% |
| B | Polymer ex. 10 | 0.80% |
| C | Water | ad 100% |
| | Citric acid | 0.30% |
| | Malic acid | 0.40% |
| | Glycolic acid | 0.70% |
| | Lactic acid | 0.70% |
| D | Fragrances | 0.30% |

Preparation
I Mix A and B
II Mix the components of C
III Add II to I
IV Stir D into I
V Homogenize emulsion, pH 3.5

Example 11

O/W Skin Milk for Dry Skin

| A | Sorbitan sesquioleate | 1.00% |
|---|---|---|
| | Mineral oil | 5.00% |
| | Isopropyl palmitate | 6.00% |
| | Jojoba oil | 2.00% |
| | Caprylic/capric triglyceride | 4.00% |
| | Soybean oil | 3.00% |
| B | Polymer ex. 13 | 1.00% |
| C | HOSTAPON ® CLG (Clariant) | 0.60% |
| | (sodium lauroyl glutamate) | |
| | AQUAMOLLIN BC powder, high-conc. (Clariant) | 0.10% |
| | (ethylenediaminetetraacetate, Na salt) | |
| | Citric acid (10% aqueous) | 2.00% |
| | Glycerol | 3.00% |
| | Water | ad 100% |
| | Preservative | q.s. |
| D | Fragrance | 0.30% |

Preparation

I Mix A and B

II Stir solution of C into I

III Add D to II

IV Homogenize emulsion

V Adjust to pH 4.8

Example 12

W/O Emulsion

Depigmenting Cream

| A | HOSTACERIN ® DGI (Clariant) | 4.00% |
|---|---|---|
| | (polyglyceryl-2 sesquiisostearate) | |
| | Cetyl alcohol | 1.20% |
| | Stearic acid | 1.00% |
| | Cetiol ® V (Henkel KGaA) | 5.00% |
| | (decyl oleate) | |
| | Beeswax | 2.00% |
| | Cyclomethicone | 7.00% |
| B | Polymer ex. 21 | 1.50% |
| | Kojic acid | 1.00% |
| | Caffeic acid | 1.00% |
| | Water | ad 100% |
| C | PEG 600 (Clariant) | 10.00% |
| | (PEG-12) | |
| | Preservative | q.s. |
| D | Fragrance | 0.40% |

Preparation

I Melt A at 80° C.

II Stir B into I

III Cool with stirring

IV Add, at 35° C., C, then D, to IV

V pH 3.4

Example 13

Clear Shower Product with Good Foam Properties

| A | GENAPOL ® LRO liquid (Clariant) | 40.00% |
|---|---|---|
| | (sodium laureth sulfate) | |
| B | Fragrance | 0.30% |
| C | Water | ad 100% |
| | Dye | q.s. |
| | Preservative | q.s. |
| | GENAGEN ® LDA (Clariant) | 6.00% |
| | (sodium lauroamphoacetate) | |
| | Citric acid | 5.00% |
| | Ascorbic acid | 0.50% |
| D | Polymer ex. 18 | 1.50% |

Preparation

I Stir B into A

II Add components of C successively to I

III Adjust pH to about 5.0

IV Adjust viscosity by stirring D into III

Example 14

Anti-Age Gel

| A | Glycerol | 3.00% |
|---|---|---|
| | Water | ad 100% |
| | Citric acid | 0.30% |
| | Malic acid | 0.40% |
| | Glycolic acid | 0.70% |
| | Lactic acid | 0.70% |
| | Preservative | q.s. |
| B | Fragrance | 0.30% |
| C | Polymer ex. 17 | 1.50% |

Preparation

I Mix A and B

II Add C to I

III Adjust pH to 5.0

Example 15

Gel with Keratolytic Effect

| A | Water | ad 100% |
|---|---|---|
| | Glycerol | 3.00% |
| | 3,6,9-Trioxaundecanedioic acid | 4.00% |
| | Preservative | q.s. |
| | Fragrance | 0.30% |
| | Polymer ex. 18 | 1.50% |

Preparation
I Mix components in succession
II Adjust to pH of 3.8

Example 16

O/W Skin Milk with Thermal-Spring Water

| | | |
|---|---|---|
| A | Polymer ex. 22 | 0.50% |
| | Polymer ex. 24 | 1.00% |
| B | Isopropyl palmitate | 4.00% |
| | Almond oil | 4.00% |
| | Wheatgerm oil | 1.00% |
| | Cetiol ® SN (Henkel) | 8.00% |
| | (cetearyl isononanoate) | |
| C | Thermal-spring water | ad 100% |
| D | Fragrances | 0.30% |
| | Preservative | 0.70% |

Preparation
I Disperse A in B with stirring
II Add C and D in succession to
III Homogenize emulsion

Example 17

O/W Face Cream

| | | |
|---|---|---|
| A | Polymer ex. 9 | 1.50% |
| | Mineral oil | 5.00% |
| | Cyclohexadimethylsiloxane | 5.00% |
| B | Magnesium ascorbyl phosphate | 0.30% |
| | Water | ad 100% |
| C | Fragrances | 0.30% |
| | Preservative | 0.70% |

Preparation
I Disperse A with stirring
II Add B and C in succession to I
III Homogenize emulsion

Example 18

Body Wash with Dead Sea Salt

| | | |
|---|---|---|
| A | GENAPOL ® LRO liquid (Clariant) | 40.00% |
| | (sodium laureth sulfate) | |
| B | Fragrance | 0.30% |
| C | Water | ad 100% |
| | Mixture of Dead Sea salt | 10.00% |
| D | Dye | q.s. |
| | Preservative | q.s. |
| | GENAGEN ® LDA (Clariant) | 6.00% |
| | (disodium lauroamphodiacetate) | |
| | Citric acid | q.s. |
| E | Polymer ex. 17 | 1.00% |

Preparation
I Stir B into A
II Mix the components of C and stir mixture into I
III Add components from D in succession to II
IV Adjust the viscosity by stirring E into III

Example 19

Sun Protection Milk

| | | |
|---|---|---|
| A | Hostaphat ® CK 100 (Clariant) | 2.00% |
| | (potassium cetyl phosphate) | |
| | Mineral oil, low viscosity | 4.00% |
| | Cetiol ® SN | 4.00% |
| | (cetearyl isononanoate) | |
| | Cetiol ® 868 | 4.00% |
| | (octyl stearate) | |
| | Neo Heliopan ® E 1000 | 8.50% |
| | (isoamyl p-methoxycinnamate) | |
| | Neo Heliopan ® BB | 8.50% |
| | (benzophenone-3) | |
| B | Polymer ex. 14 | 1.00% |
| C | Water | ad 100% |
| | Hostapon ® CCG (Clariant) | 0.60% |
| | (sodium cocoylglutamate) | |
| | Allantoin (Clariant) | 0.30% |
| | Allantoin | |
| | Glycerol | 5.00% |
| | Panthenol | 1.00% |
| D | Fragrance | 0.30% |
| | Phenonip ® (Clariant) | 0.50% |
| | Phenoxyethanol (and) methylparaben (and) butylparaben | |
| | (and) ethylparaben (and) propylparaben | |

Preparation
I Melt A, then add B
II Heat C to 80° C.
III Stir II into I and cool with stirring
IV Add D to III at 35° C.
V Homogenize the emulsion

Example 20

Clear Antidandruff Shampoo with UV Protection

| | | |
|---|---|---|
| A | Octopirox ® (Clariant) | 0.50% |
| | (piroctone olamine) | |
| B | Water | 10.00% |
| | Polymer ex. 24 | 0.70% |
| C | Genapol ® LRO liquid (Clariant) | 30.00% |
| | (sodium laureth sulfate) | |
| | Benzophenone-1 | 0.50% |
| D | Fragrance | 0.30 |
| E | Allantoin (Clariant) | 0.30 |
| F | Water | ad 100% |
| G | Dye solution | q.s. |
| | Panthenol | 1.00% |
| | Extrapone Nettle Special | 2.00% |
| | (Urtica Dioica (nettle) extract) | |
| | Genagen ® CAB (Clariant) | 8.00% |

Preparation
I Mix A with B
II Add C to I and stir until solution clears
III Stir components D successively into II
IV Dissolve E in F with stirring and gentle heating, and add to III with stirring
V Stir components G into IV
VI Adjust the pH

The invention claimed is:
1. A polymer comprising
a) at least one structural repeat unit of the formula (1)

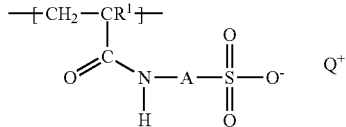

(1)

wherein $R^1$ is hydrogen, methyl or ethyl and A is $C_1$-$C_8$-alkylene, and $Q^+$ is $H^+$, $NH_4^+$, $Li^+$, $Na^+$, $K^+$, ½ $Ca^{++}$, ½ $Mg^{++}$, ½ $Zn^{++}$ or ⅓ $Al^{+++}$, and the degree of neutralization of the structural units of the formula (1) is from 50 to 100 mol %,
and
b) at least one structural repeat unit of the formula (2)

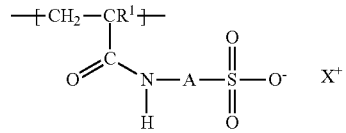

(2)

wherein $R^1$ and A have the definition of $R^1$ and A from formula (1) and $X^+$ is selected from the group consisting of laurylamidopropyldimethylammonium, stearylamidopropyldimethylammonium, behenylamidopropyldimethylammonium, $C_{12-18}$-alkyldimethylammonium, and $C_{20}$-$C_{22}$-alkyldimethylammonium ion,
with the proviso that the molar ratio of the structural units of the formula (1) in which $Q^+$ is $NH_4^+$, $Li^+$, $Na^+$, $K^+$, $Ca^{++}$, $Mg^{++}$, $Zn^{++}$ or $Al^{+++}$ to the structural units of the formula (2) is from 97:3 to 55:45, and a corresponding alkylammonium chloride having a critical micelle concentration (CMC) <15 g/l,
and
d) 0% to 8% by weight based on the total weight of the polymer of crosslinking structural units originating from monomers having at least two olefinic double bonds.
2. The polymer as claimed in claim 1, comprising
ab) 49.99% to 98.99% by weight based on the total weight of the polymer of a mixture of the structural repeat units of the formulae (1) and (2),
c1) 1% to 50% by weight based on the total weight of the polymer of the structural repeat units of the formula (3)

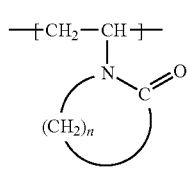

(3)

where n is an integer from 2 to 9,
or
c2) 1% to 50% by weight based on the total weight of the polymer of a mixture of the structural repeat unit of the formula (3) and the structural repeat unit of the formula (4)

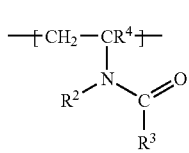

(4)

where $R^2$ and $R^3$ are alike or different and are hydrogen or a linear or branched alkyl group having 1 to 22 carbon atoms or a linear or branched, singly or multiply unsaturated alkenyl group having 2 to 22 carbon atoms, and $R^4$ is hydrogen, methyl or ethyl,
and
d) 0% to 8% by weight based on the total weight of the polymer of crosslinking structural units originating from monomers having at least two olefinic double bonds.
3. The polymer as claimed in claim 1, comprising
ab) 92% to 99.99% by weight based on the total weight of the polymer of a mixture of the structural repeat units of the formulae (1) and (2) and
d) 8% to 0.01% by weight based on the total weight of the polymer of crosslinking structural units originating from monomers having at least two olefinic double bonds.
4. The polymer as claimed in claim 2, comprising
69.5% to 97.5% by weight based on the total weight of the polymer of a mixture of the structural units of the formulae (1) and (2),
2% to 30% by weight based on the total weight of the polymer of the structural units of the formula (3) or of a mixture of the structural units of the formulae (3) and (4),
and
0.2% to 3% by weight based on the total weight of the polymer of crosslinking structural units originating from monomers having at least two olefinic double bonds.
5. The polymer as claimed in claim 1, wherein the structural units of the formulae (1) and (2) are derived from 2-acrylamido-2-methylpropanesulfonic acid.
6. The polymer as claimed in claim 2, wherein the structural units of the formula (3) are derived from N-vinylpyrrolidone.
7. A polymer as claimed in claim 1, wherein $R^2$ and $R^3$ in the structural units of the formula (4) are hydrogen or methyl and $R^4$ is hydrogen.
8. The polymer as claimed in claim 1, wherein the non-$H^+$ counterion $Q^+$ in the structural units of the formula (1) is selected from the group consisting of $NH_4^+$, alkali metal$^+$, and alkaline earth metal$^{++}$.
9. A process for preparing a polymer as claimed in claim 1, comprising the steps of
i) dispersing or dissolving monomers from which the structural units of the formulae (1) and (2) derive, and additionally, if desired, monomers from which the structural units of the formula (3) or of the formulae (3) and (4) derive, in a protic solvent,
ii) neutralizing the dispersion or solution from step i) with ammonia or with a base containing $Li^+$, $Na^+$, $K^+$, $Ca^{++}$, $Mg^{++}$, $Zn^{++}$ or $Al^{+++}$, and with an alkylamine,
iii) optionally, adding one or more crosslinkers having at least two olefinic double bonds to the neutralized dispersion or solution from step ii) and iv) initiating the polymerization by adding a free-radical-forming compound.

10. A thickener, bodying agent, emulsifier, sensorial additive, solubilizer, dispersant, lubricant, adhesive or stabilizer composition, comprising at least one polymer as claimed in claim 1.

11. A thickener, bodying agent, emulsifier, sensorial additive, solubilizer, dispersant, lubricant, adhesive or stabilizer composition as claimed in claim 10 having an oil fraction of >5% by weight, based on the completed composition.

12. A cosmetic, pharmaceutical or dermatological composition comprising at least one polymer as claimed in claim 1.

13. A composition as claimed in claim 12, wherein the composition is in the form of a fluid, gel, oil, foam, spray, lotion or cream.

14. A composition as claimed in claim 12, wherein the composition is in the form of an oil-in-water emulsion containing no emulsifiers or surfactants.

15. A composition as claimed in claim 12, wherein the composition has a pH of 2 to 6.5.

16. A composition as claimed in claim 12, wherein the composition further comprises at least one electrolyte.

17. A composition as claimed in claim 12, wherein the composition is in the form of a sunscreen composition and further comprises one or more sun protection filters for protecting the hair and the skin from UV rays.

* * * * *